United States Patent
Yang et al.

(10) Patent No.: US 8,600,497 B1
(45) Date of Patent: Dec. 3, 2013

(54) SYSTEMS AND METHODS TO MONITOR AND TREAT HEART FAILURE CONDITIONS

(75) Inventors: Weiqun Yang, Cupertino, CA (US); Malin Ohlander, Stockholm (SE); Louis Wong, Sunnyvale, CA (US); Nils Holmstrom, Jarfalla (SE); Cem Shaquer, San Jose, CA (US); Euljoon Park, Valencia, CA (US); Dorin Panescu, San Jose, CA (US); Shahrooz Shahparnia, Campbell, CA (US); Andre Walker, Monte Sereno, CA (US); Ajit Pillai, Sunnyvale, CA (US); Mihir Naware, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 1440 days.

(21) Appl. No.: 11/558,088

(22) Filed: Nov. 9, 2006

Related U.S. Application Data

(60) Provisional application No. 60/787,884, filed on Mar. 31, 2006.

(51) Int. Cl.
*A61B 5/05* (2006.01)
*A61N 1/00* (2006.01)

(52) U.S. Cl.
USPC .......... 607/7; 607/8; 607/18; 607/20; 607/24; 607/28; 600/547

(58) Field of Classification Search
USPC ................. 600/547; 607/7, 8, 18, 20, 24, 28
See application file for complete search history.

(56) References Cited

U.S. PATENT DOCUMENTS

| | | | |
|---|---|---|---|
| 3,934,458 A | 1/1976 | Beretsky | |
| 4,535,774 A | 8/1985 | Olson | |
| 4,686,987 A | 8/1987 | Salo et al. | |
| 5,003,976 A | 4/1991 | Alt | |
| 5,042,303 A | 8/1991 | Geluk | |
| 5,179,946 A | 1/1993 | Weiss | |

(Continued)

FOREIGN PATENT DOCUMENTS

| WO | WO 96/15827 | 5/1996 |
|---|---|---|
| WO | WO 96/19260 | 6/1996 |

(Continued)

OTHER PUBLICATIONS

Non-Final Office Action mailed Jun. 10, 2009: Related U.S. Appl. No. 11/684,677.

(Continued)

*Primary Examiner* — Joseph Stoklosa
*Assistant Examiner* — Lindsey G Hankins
(74) *Attorney, Agent, or Firm* — Steven M. Mitchell

(57) ABSTRACT

An implantable device monitors and treats heart failure, pulmonary edema, and hemodynamic conditions and in some cases applies therapy. In one implementation, the implantable device applies a high-frequency multi-phasic pulse waveform over multiple-vectors through tissue. The waveform has a duration less than the charging time constant of electrode-electrolyte interfaces in vivo to reduce intrusiveness while increasing sensitivity and specificity for trending parameters. The waveform can be multiplexed over multiple vectors and the results cross-correlated or subjected to probabilistic analysis or thresholding schemata to stage heart failure or pulmonary edema. In one implementation, a fractionation morphology of a sensed impedance waveform is used to trend intracardiac pressure to stage heart failure and to regulate cardiac resynchronization therapy. The waveform also provides unintrusive electrode integrity checks and 3-D impedancegrams.

24 Claims, 32 Drawing Sheets

(56) References Cited

U.S. PATENT DOCUMENTS

| | | | |
|---|---|---|---|
| 5,190,035 | A | 3/1993 | Salo et al. |
| 5,201,865 | A | 4/1993 | Kuehn |
| 5,282,840 | A | 2/1994 | Hudrlik |
| 5,300,093 | A | 4/1994 | Koestner et al. |
| 5,324,309 | A | 6/1994 | Kallok |
| 5,344,429 | A | 9/1994 | Smits |
| 5,507,785 | A | 4/1996 | Deno |
| 5,531,772 | A | 7/1996 | Prutchi |
| 5,713,935 | A | 2/1998 | Prutchi |
| 5,746,214 | A * | 5/1998 | Brown et al. ............... 600/547 |
| 5,800,467 | A | 9/1998 | Park |
| 5,814,088 | A | 9/1998 | Paul |
| 5,957,861 | A | 9/1999 | Combs |
| 6,044,294 | A * | 3/2000 | Mortazavi et al. ............ 600/547 |
| 6,198,965 | B1 | 3/2001 | Penner |
| 6,219,579 | B1 | 4/2001 | Bakels |
| 6,223,082 | B1 | 4/2001 | Bakels |
| 6,251,303 | B1 | 6/2001 | Bawendi |
| 6,269,264 | B1 | 7/2001 | Weyant |
| 6,275,727 | B1 | 8/2001 | Hopper et al. |
| 6,278,894 | B1 | 8/2001 | Salo et al. |
| 6,337,994 | B1 | 1/2002 | Stoianovici |
| 6,339,722 | B1 | 1/2002 | Heethaar |
| 6,459,929 | B1 | 10/2002 | Hopper et al. |
| 6,473,640 | B1 * | 10/2002 | Erlebacher ................... 600/547 |
| 6,473,647 | B1 | 10/2002 | Bradley |
| 6,501,983 | B1 | 12/2002 | Natarajan |
| 6,512,942 | B1 | 1/2003 | Burdette |
| 6,512,949 | B1 * | 1/2003 | Combs et al. ................ 600/547 |
| 6,527,729 | B1 | 3/2003 | Turcott |
| 6,539,261 | B2 | 3/2003 | Dal Molin |
| 6,595,927 | B2 | 7/2003 | Pitts-Crick et al. |
| 6,620,186 | B2 | 9/2003 | Saphon |
| 6,754,530 | B2 | 6/2004 | Bakels |
| 6,970,742 | B2 | 11/2005 | Mann |
| 7,010,347 | B2 | 3/2006 | Schecter |
| 7,065,400 | B2 * | 6/2006 | Schechter ........................ 607/2 |
| 7,065,403 | B1 | 6/2006 | Mouchawar |
| 7,139,610 | B2 * | 11/2006 | Ferek-Petric ................. 607/27 |
| 7,184,821 | B2 * | 2/2007 | Belalcazar et al. ............ 600/547 |
| 7,200,442 | B1 | 4/2007 | Koh |
| 7,272,443 | B2 * | 9/2007 | Min et al. ...................... 607/17 |
| 7,410,467 | B2 | 8/2008 | Cooper |
| 2001/0051774 | A1 | 12/2001 | Littrup |
| 2002/0002389 | A1 | 1/2002 | Bradley |
| 2003/0083712 | A1 | 5/2003 | Rueter |
| 2003/0220556 | A1 | 11/2003 | Porat |
| 2004/0015196 | A1 | 1/2004 | Holmstrom |
| 2004/0059220 | A1 | 3/2004 | Mourad |
| 2004/0064161 | A1 | 4/2004 | Gunderson |
| 2004/0215097 | A1 * | 10/2004 | Wang ............................. 600/547 |
| 2004/0220640 | A1 * | 11/2004 | Burnes et al. .................. 607/28 |
| 2004/0230112 | A1 | 11/2004 | Scholz |
| 2005/0021103 | A1 * | 1/2005 | DiLorenzo ..................... 607/45 |
| 2005/0124908 | A1 * | 6/2005 | Belalcazar et al. ............ 600/547 |
| 2005/0215914 | A1 | 9/2005 | Bornzin |
| 2005/0216067 | A1 * | 9/2005 | Min et al. ...................... 607/17 |
| 2005/0283091 | A1 * | 12/2005 | Kink et al. .................... 600/547 |
| 2006/0025828 | A1 | 2/2006 | Armstrong |
| 2006/0129196 | A1 * | 6/2006 | Dong et al. .................... 607/28 |
| 2006/0135886 | A1 | 6/2006 | Lippert |
| 2006/0184060 | A1 * | 8/2006 | Belalcazar et al. ........... 600/547 |
| 2006/0235480 | A1 * | 10/2006 | Schecter ........................ 607/18 |
| 2006/0241512 | A1 | 10/2006 | Kwok |
| 2006/0293609 | A1 | 12/2006 | Stahmann |
| 2008/0221477 | A1 | 9/2008 | Olson et al. |

FOREIGN PATENT DOCUMENTS

| | | |
|---|---|---|
| WO | WO 98/07467 | 2/1998 |
| WO | 0113792 A1 | 3/2001 |
| WO | 0132260 A1 | 5/2001 |
| WO | WO 01/87410 A2 | 11/2001 |
| WO | WO 01/87410 A3 | 11/2001 |
| WO | 2004096041 A2 | 11/2004 |
| WO | 2004096041 A3 | 11/2004 |
| WO | WO2004105862 | 12/2004 |
| WO | WO 2004105862 A2 * | 12/2004 |

OTHER PUBLICATIONS

Non-Final Office Action mailed May 27, 2009: Related U.S. Appl. No. 11/684,681.

Non-Final Office Action mailed Apr. 6, 2009: Related U.S. Appl. No. 11/558,101.

Non-Final Office Action mailed Feb. 3, 2009: Related U.S. Appl. No. 11/557,851.

Non-Final Office Action mailed May 29, 2009: Related U.S. Appl. No. 11/557,870.

Non-Final Office Action mailed Jun. 10, 2009: Related U.S. Appl. No. 11/557,882.

Final Office Action mailed Jan. 25, 2010: Related U.S. Appl. No. 11/684,664.

Final Office Action mailed Jan. 21, 2010: Related U.S. Appl. No. 11/684,677.

Final Office Action mailed Feb. 3, 2010: Related U.S. Appl. No. 11/684,681.

Non-Final Office Action mailed Aug. 20, 209: Related U.S. Appl. No. 11/684,688.

Final Office Action mailed Jan. 21, 2010: Related U.S. Appl. No. 11/684,688.

Final Office Action mailed Oct. 8, 2009: Related U.S. Appl. No. 11/558,101.

Advisory Action mailed Feb. 4, 2010: Related U.S. Appl. No. 11/558,101.

Final Office Action mailed Nov. 13, 2009: Related U.S. Appl. No. 11/557,851.

Advisory Action mailed Feb. 22, 2010: Related U.S. Appl. No. 11/557,851.

Final Office Action mailed Mar. 3, 2010: Related U.S. Appl. No. 11/557,870.

Non-Final Office Action mailed Sep. 15, 2009: Related U.S. Appl. No. 11/559,235.

Stutz, "All About Circuits: Conductance." Copyright 1999-2000. <http://www.allaboutcircuits.com/vol_1/chpt_5/4.html>.

Non-Final Office Action mailed Jun. 19, 2009 Related U.S. Appl. No. 11/684,664.

Non-Final Office Action mailed Jun. 22, 2009 Related U.S. Appl. No. 11/684,670.

* cited by examiner

Different Impedance Measurement Configurations

| 150 | 500 |

LV - RV OHM (INCORRECT)    LV - RV OHM (CORRECT)

Fig. 26

SYSTEMS AND METHODS TO MONITOR AND TREAT HEART FAILURE CONDITIONS

RELATED APPLICATIONS

This application is related to U.S. Provisional Patent Application No. 60/787,884 to Wong et al., entitled, "Tissue Characterization Using Intracardiac Impedances with an Implantable Lead System," filed Mar. 31, 2006, and incorporated herein by reference.

APPENDIX LISTING

A listing referred to as Appendix A of electrode combinations for creating electrical vectors is provided beginning on a separate sheet, on two sheets of paper and incorporated by reference into the specification.

TECHNICAL FIELD

Subject matter presented herein relates generally to implantable medical devices and more particularly to systems and methods to monitor and treat heart failure conditions.

BACKGROUND

Conventional implantable medical devices often obtain a rough measure of physiological parameters by sensing variation in voltage or other electrical characteristics along a single electrical path, field, or vector. For example, as shown in FIG. 1, such may be used to acquire rough impedance values that allow the implantable device to track a patient's respirations, since thoracic impedance varies with breathing. Energy transferred between a tip electrode and a case electrode typically provides a general-purpose electrical pathway or vector 100 consisting of electrons traveling pathways of least resistance or least impedance. Often, this technique produces some useful data in relation to the degree that the electrical vector achieved approximates a relevant vector orientation for measuring the target parameter. Tracking a physiological parameter is often correlated to a specific condition, such as respiration rate.

Congestive heart failure (CHF) or just "heart failure," is a condition in which a patient's heart works less efficiently than it should, and in which the heart pumps insufficiently thereby depriving the body of the oxygen-carrying blood it requires, either during exercise or at rest. To compensate for this condition and to maintain cardiac output, the body retains sodium and water such that there is a build-up of fluid hydrostatic pressure in the pulmonary blood vessels that drain the lungs. As this hydrostatic pressure overwhelms oncotic pressure and lymph flow, fluid transudates from the pulmonary veins into the pulmonary interstitial spaces, and eventually into the alveolar air spaces. This complication of CHF is called pulmonary edema (PE), which can cause hypoxemia, respiratory acidosis, respiratory arrest, and death.

Similarly, CHF often involves dangerous decreases in chamber ejection fractions and enlargement of the ventricles and atria. Left atrial (LA) enlargement can result in atrial fibrillation. Left ventricular (LV) enlargement can result in ventricular tachycardias. Typically, known as ventricular dyssynchrony, the normal "V-V" delay between right ventricular contraction and left ventricular contraction is unduly lengthened during heart failure, further reducing pumping efficiency. Additionally, delays may appear between the electrical stimulation provided during the QRS complex of the cardiac cycle and the timing of the mechanical contraction that results from this electrical stimulation. These conditions typify the many adverse effects of heart failure that cause a viscous circle of failure: reduced efficiency begets attempts by the heart to compensate for the loss, but the compensation ultimately leads to further loss of efficiency, and so on. Therapy seeks to intervene before a point of no return is reached in the viscous circle.

At times the conventional implantable medical devices introduced above, in trying to track physiological parameters, can produce inaccurate data, false positives, and false negatives with respect to pathophysiological conditions like CHF. A false positive indicates the presence of a condition that does not really exist—because the conventional technique measures a parameter that is partly or entirely different than the target parameter, i.e., the specificity of the impedance measurement with regard to the parameter being measured is low. Conversely, a false negative indicates the absence of a condition that really is present—again, because the conventional technique measures a parameter that is different than that intended, or, because sensitivity to the parameter being measured is low.

Often conventional techniques examine a pathway of tissue in the body that is too limited or too unrelated to the parameter being measured—the parameters or conditions being measured are partly beyond the scope of the electrical pathway being utilized. The pathway may be limited because it is poorly selected with regard to the parameter sought, or because the same pathway is always used to measure many different kinds of diverse parameters, even parameters that are only tangentially related to the pathway. Using such a single general purpose vector has its limits and can even return misleading information, as just described.

SUMMARY

Described are systems and methods to monitor and treat heart failure conditions. In one implementation, an implantable device applies a high-frequency multi-phasic pulse waveform over at least one vector (pathway) through bodily tissue and then measures resulting impedance effects. The impedance effects correlate to one or more bodily parameters (i.e., physiological parameters, including hemodynamic parameters). One or more of these parameters, in turn, can be trended to track the course of heart failure and/or to regulate heart failure therapy. The terms "trending" or "trended" as used herein refer to tracking, following, or just recording values (or estimates of values) of a parameter over time, not to controlling the parameter itself by creating a trend in the parameter (e.g., through therapy). Because the applied waveform is charge-balanced, voltage-balanced, and has a duration less than the charging time constant of electrode-electrolyte interfaces in vivo, the impedance effects resulting from the waveform's application provide a wealth of probative detail for determining values of the relevant parameters. For example, various shape (morphology) characteristics of a sensed impedance waveform can be used to produce or trend an estimator of an intracardiac pressure parameter. The estimator or trend is then used to stage heart failure or to regulate cardiac resynchronization therapy (CRT).

Because of its features, the applied waveform minimizes the intrusiveness that is usually associated with applied pulses. That is, the patient may not perceive application of the waveform, and its application typically does not alter the parameter being measured, as is often the case when conventional pulses are applied.

Further, the applied waveform can be time-multiplexed or frequency-multiplexed in its application over multiple vectors through a bodily tissue. The multiplexing of multiple instances of the applied waveform over multiple vectors provides unprecedented selectivity and specificity in tracking and trending parameters useful for regulating heart failure therapies. Thus, in one implementation, the implantable device designates, or is hardwired to create, a multi-vector network that may include at least one intracardiac vector. Multiple impedances measured over different vectors of such a multi-vector network are submitted to multi-vector data processing. This processing can take the form of cross-correlation or application of a cross co-variance function. In one instance, cross-correlation aims to find a similarity (or dissimilarity) of the multiple signals, for example, to find a value or feature in an unknown or deviant impedance signal by comparing it to one or more known signals. Or, the multi-vector data processing may take the form of statistical or probabilistic decision making. Yet again, the multi-vector data processing may be submitted to thresholding schemata. These and other data processing techniques may be leveraged to establish an accurate and reliable value for a data point of a parameter being estimated or trended. The multiplexed waveform enables simultaneous, quasi-simultaneous, and/or sequential impedance measurements over the multiple vectors to provide the multiple signals for such multi-vector data processing.

The system can detect tissue swelling, such as fluid accumulation or edema—even at early onset—with greater selectivity as to location of the tissue swelling and greater specificity that the condition being sensed is really tissue swelling or fluid accumulation and not some other condition with a similar impedance effect.

In an alternative implementation, the implantable device leverages the waveform to check lead integrity, electrode integrity, and/or lead-to-device integrity without applying pulses that are disturbing to the patient.

In another alternative implementation, the implantable device leverages the waveform to generate vector-impedancegrams to locate problems or to visualize tissue differences and even lesions that can be discernible on a vector-impedancegram.

BRIEF DESCRIPTION OF THE DRAWINGS

FIG. 26 is a diagram of an exemplary test technique for lead connectivity to a device header.

DETAILED DESCRIPTION

Overview

Figure 1:
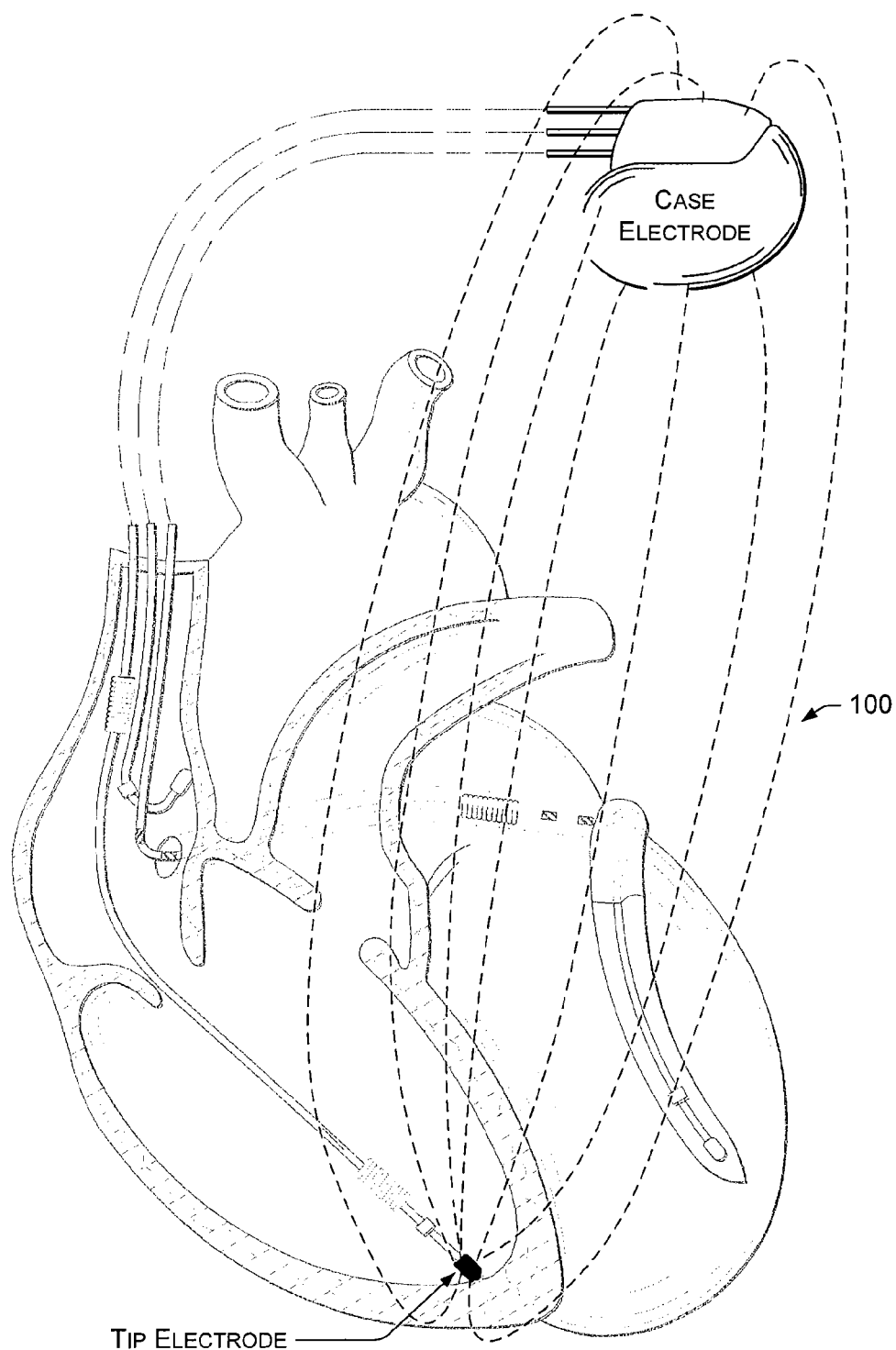
FIG. 1 is a diagram of a conventional general purpose electrical vector utilized by an implantable device.

This disclosure describes systems and methods to monitor and treat heart failure conditions. As described below, an exemplary implantable device applies a high-frequency multi-phasic pulse waveform over at least one vector through bodily tissue and then measures resulting impedance effects. The impedance effects correlate to one or more physiological or hemodynamic parameters. One or more of these parameters, in turn, can be trended to track the course of heart failure and/or to regulate heart failure therapy. Because the applied waveform is charge-balanced, voltage-balanced, and has a duration less than the charging time constant of electrode-electrolyte interfaces in vivo, the impedance effects resulting from the waveform's application provide a wealth of probative detail for determining values of the relevant parameters used for monitoring and treating heart failure.

The implantable device measures impedance effects resulting from the applied waveform, over one or more vectors through (or at least related to) the bodily tissue. The impedance effects may include, for example, various components of a raw sensed impedance and/or may include features of the shape (morphology) of the sensed impedance waveform. The measured impedance effects correspond to the current state of one or more selected bodily parameters that are related to monitoring or treating heart failure. The relevant bodily parameters may be physiological parameters such as tissue swelling, fluid accumulation, edema, etc., or may be hemodynamic parameters, such as intracardiac pressure, left ventricular ejection fraction (LVEF), and many others. One or more of these parameters, in turn, can be trended over time (or can be used directly as a single data point) to track the course of heart failure and/or to regulate heart failure therapy (such as CRT).

Additionally, because of its features, the applied waveform minimizes intrusiveness that is usually associated with conventional applied pulses that can be felt by a patient. Likewise, the applied waveform typically does not alter the value of the parameter being measured, as is often the case when conventional pulses are applied.

Further, the applied waveform can be time-multiplexed or frequency-multiplexed in its application over multiple vectors through a bodily tissue. Multiplexing multiple instances of the applied waveform over multiple vectors provides unprecedented selectivity and specificity in tracking and trending parameters useful for regulating heart failure therapies. Thus, in one implementation, the implantable device designates or is hardwired to create a multi-vector network that in some instances includes at least one intracardiac vector. Multiple impedances measured over different vectors of such a multi-vector network can be cross-correlated, e.g., by a probability engine, to establish an accurate and reliable value for a data point of a parameter being trended. The multiplexed waveform enables simultaneous, quasi-simultaneous, and/or sequential impedance measurements over the multiple vectors. In some cases, because the applied waveform creates rich impedance waveform effects, only one vector need be employed for many of the types of parameters to be trended, When a multi-vector network system is used instead of a single vector, the multi-vector system can receive information from multiple simultaneous or sequential impedance vectors to improve the accuracy of determining heart hemodynamics, predicting heart failure by detecting changing pressure or ejection fractions, or structural heart changes, such as left atrial (LA) and/or left ventricular (LV) enlargement, right ventricular (RV) enlargement, etc.

The system can detect tissue swelling, such as fluid accumulation or edema—even at early onset—with greater selectivity as to location of the tissue swelling and with greater specificity that the condition being sensed is really tissue swelling or fluid accumulation and not some other condition with a similar impedance effect.

In one implementation, an exemplary implantable device senses impedance effects and trends corresponding bodily parameters over time in order to monitor and treat heart failure. In another implementation, the exemplary implantable device transfers values externally, e.g., to an external programmer, so that the trending can be performed on the external device, which may have more computing power than the implantable device.

In an alternative implementation, the implantable device leverages the waveform to check lead integrity, electrode integrity, and/or lead-to-device integrity without applying pulses that are disturbing to the patient. Thus the systems to be described below use the applied waveform to improve routine maintenance tasks in and around an implantable device as well as to optimize cardiac therapies.

In another alternative implementation, the implantable device leverages the waveform to generate vector-impedancegrams to locate problems or to visualize tissue differences and even lesions within the catchment volume of a multi-vector network.

Exemplary Electrode Configurations

Conventional implantable lead systems as well as custom lead systems usually have numerous electrodes that can be selected in combination to create the multi-vector networks. For example, many conventional lead systems have at least 9-11 available electrodes, implemented as tip, coil, ring, and broad surface area electrodes, that is:

the CASE electrode
Right Ventricular coil (RV-c) electrode
Superior Vena Cava (SVC) coil electrode
Right Atrial ring electrode (RA-r)
Right Ventricular ring electrode (RV-r)
Left Ventricular ring electrode (LV-r)
Right Atrial tip electrode (RA-t)
Right Ventricular tip electrode (RV-t)
Left Ventricular tip electrode (LV-t)
Left Atrial ring electrode (LA-r)
Left Atrial tip electrode (LA-t).

These electrodes, discussed more fully below, are typically included in many implantable lead systems.

A related feature of the multi-vector network is that multiple vectors can be selected, rearranged, or unselected by configuring electrode combinations. Selected vectors are customizable.

Figure 2:
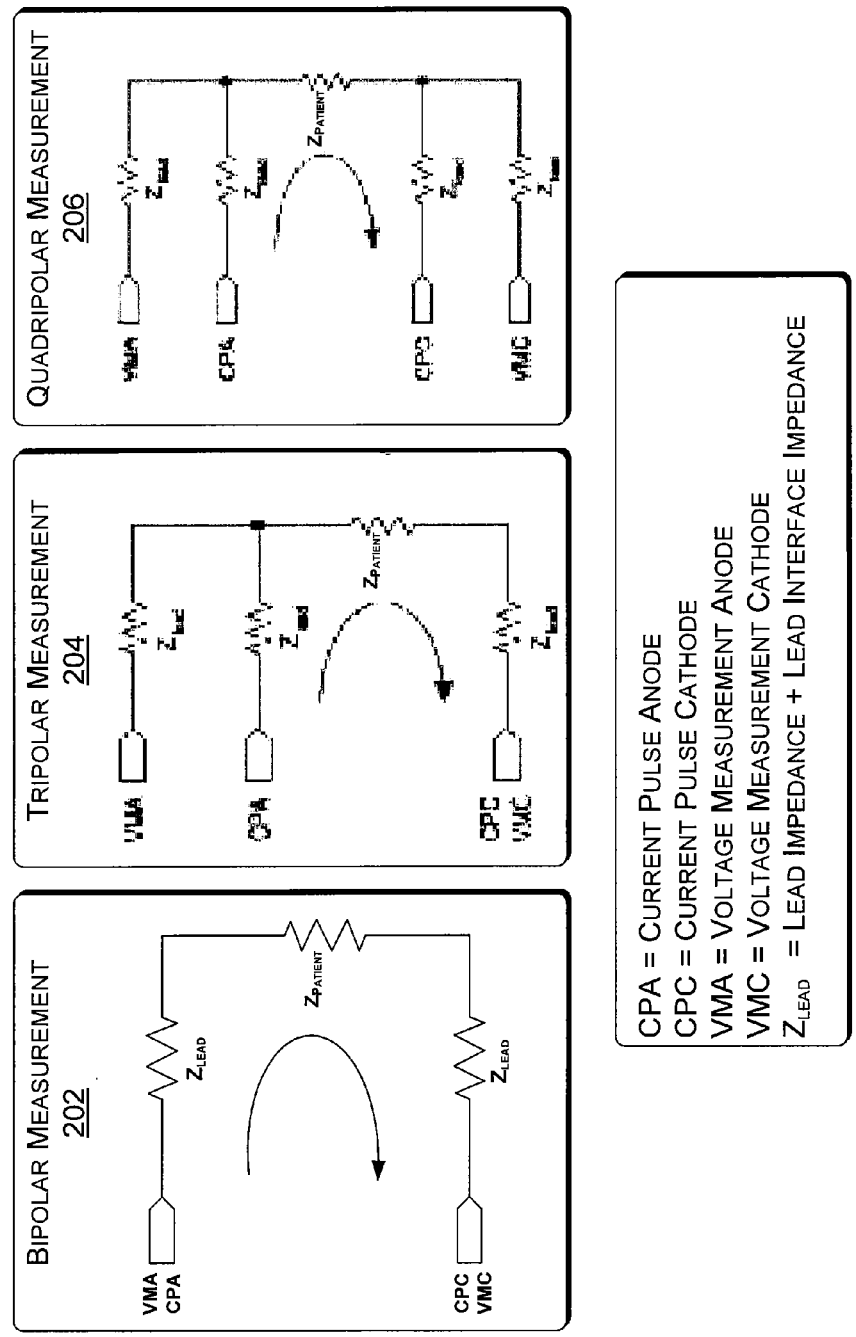
FIG. 2 is a diagram of different impedance measurement electrode configurations.

FIG. 2 shows various electrode configurations for measuring impedance, e.g., across a pathway of bodily tissue. Any of these impedance measurement configurations can be used to achieve a given vector of the multi-vector network. Thus, when measuring impedance, the measurement itself does not have to be obtained from the same set of leads as is used for applying the signal (pulses or waveforms). Bipolar 202 (two node measurement), tripolar 204 (three node measurement), and quadripolar 206 (four node measurement) configurations can be used within an exemplary multi-vector network.

When the various electrode configurations of FIG. 2 are applied across various electrode combinations, e.g., combinations of the eleven electrodes listed above, a selection of 1296 electrode combinations results that can be utilized in a multi-vector network. That is, the different impedance measurement electrode configurations can be used for each selected vector of a given multi-vector network. If even more electrodes are used in a particular lead system than the conventional electrodes and case associated with a typical 3-lead implantation, or if combinations are customized, or if combinations of combinations are used, then the number of electrode combinations that can be used in an exemplary multi-vector network increases dramatically.

The term "multi-vector network" means that a given measurement is simultaneously, quasi-simultaneously, or sequentially acquired over multiple electrical pathways, or more specifically, by multiple different sets of electrodes "aimed" from different perspectives at the same parameter, structure, or condition being measured. "Simultaneously acquired" means that multiple measurements made over multiple vectors are acquired at the same time in some implementations, or in rapid succession (quasi-simultaneously) in other implementations such that the speed of the rapid succession is fast enough that the elapsed time between each measurement in a single set of vector measurements is dismissible for purposes of associating the multiple measurements with the same temporal data point. Depending on probability processors, filters, and/or logic blocks incorporated into various implementations, the network of measurements can be combined into one "high quality" measurement, or, the network of measurements can be regarded as a set of separate related measurements that give a far better picture of the state of the parameter, structure, or condition being sensed or measured.

In some implementations, the multi-vector network uses exemplary waveforms to probe bodily conditions. The exemplary waveforms are designed with many features favorable for probing tissues and measuring physiological conditions inside the human body. For example, an exemplary vector may use electrical waveforms such as those described in U.S. Patent Application No. 60/787,884 to Wong et al, entitled, "Tissue Characterization Using Intracardiac Impedances with an Implantable Lead System," filed Mar. 31, 2006, and incorporated herein by reference in its entirety. In various implementations, an implantable device injects pulses inside the body that have the exemplary electrical waveform and electrically senses the results. As used herein, "inject" will be used to mean sending an electrical signal from a circuit of the implantable device into human tissue, e.g., applying via an electrode.

Multi-Vector Impedance Measurements

The exemplary methods and systems described herein acquire and process multi-vector data, such as impedance data, with the purpose of improving the specificity and sensitivity of sensing, diagnosing, and/or trending conditions associated with the early onset of heart failure. Such conditions include, for example, subtle hemodynamic changes that typically precede more overt symptoms such as pulmonary edema, etc. An implantable device using the exemplary multi-vector network detects the onset of heart failure earlier than conventional systems.

The multi-vector systems to be described in more detail further below can often resolve the following problems and/or offer the following advantages:

Multiple impedance vectors can be evaluated and/or weighted according to various schemata in order to cross-correlate the vectors, thereby reinforcing accuracy and specificity of measurements and/or providing supplemental information.

Because of greater availability of vectors and greater flexibility in their selection and combination, relevant vectors can be matched more accurately to particular bodily conditions.

A set of vectors comprising a particular multi-vector network can be adaptively optimized—"tailored" —by pruning and grafting vectors.

Redundancy between multiple vectors can help eliminate measurements that are errant beyond a threshold.

A 3-dimensional impedance cardiographic view of tissues or bodily structures can sometimes be achieved by combining multiple sensing vectors.

Different sets of multiple vectors can be adaptively applied to the same tissue or bodily structure to gather the best data.

Data from the multiple vectors of a given multi-vector network can be gathered simultaneously, quasi-simultaneously in near real-time, or sequentially.

The features enumerated above, and other features of exemplary multi-vector impedance measurement are applied to improve diagnosis and treatment of many diseases and practical problems including:

Information from several impedance vectors can be cross-correlated to improve the accuracy of detecting fluid build-up in the lungs.

Information from several impedance vectors can be used to improve the accuracy of predicting worsening heart hemodynamics, such as increasing pressure, increasing ventricular dyssynchrony and decreasing ejection fraction, or structural heart changes, such as LA and/or LV enlargement, RV enlargement.

The systems can often be implemented in hardware suitable for long-term implantable devices, because in many implementations the systems often do not require specialized sensors.

The methods and systems can be used to monitor the integrity of the implanted device lead system and detect conditions outside normal operating ranges.

The systems are likely to increase a patient's safety, because the systems provide better information to the practitioner.

As introduced above, various electrode combinations can be used to acquire impedance. In one implementation, an implantable system measures the impedance across multiple implanted electrodes that are located inside the heart, on the epicardium of the heart, or within the thorax. Sometimes, possible electrode combinations, giving rise to one or more electrical vectors, can include logical and virtual endpoints—or "calculated leads." That is, similarly to the known concept of vector electrocardiography—which provides a virtual representation of the electrical activity of the heart, combination of several physical impedance vectors can describe a virtual representation of the mechanical activity of the heart.

Exemplary Lead System and Exemplary Implantable Device

Before further describing exemplary systems and methods to monitor and treat heart failure conditions, an exemplary lead system and implantable device are now described to provide an example environment for hosting the subject matter.

Figure 3:
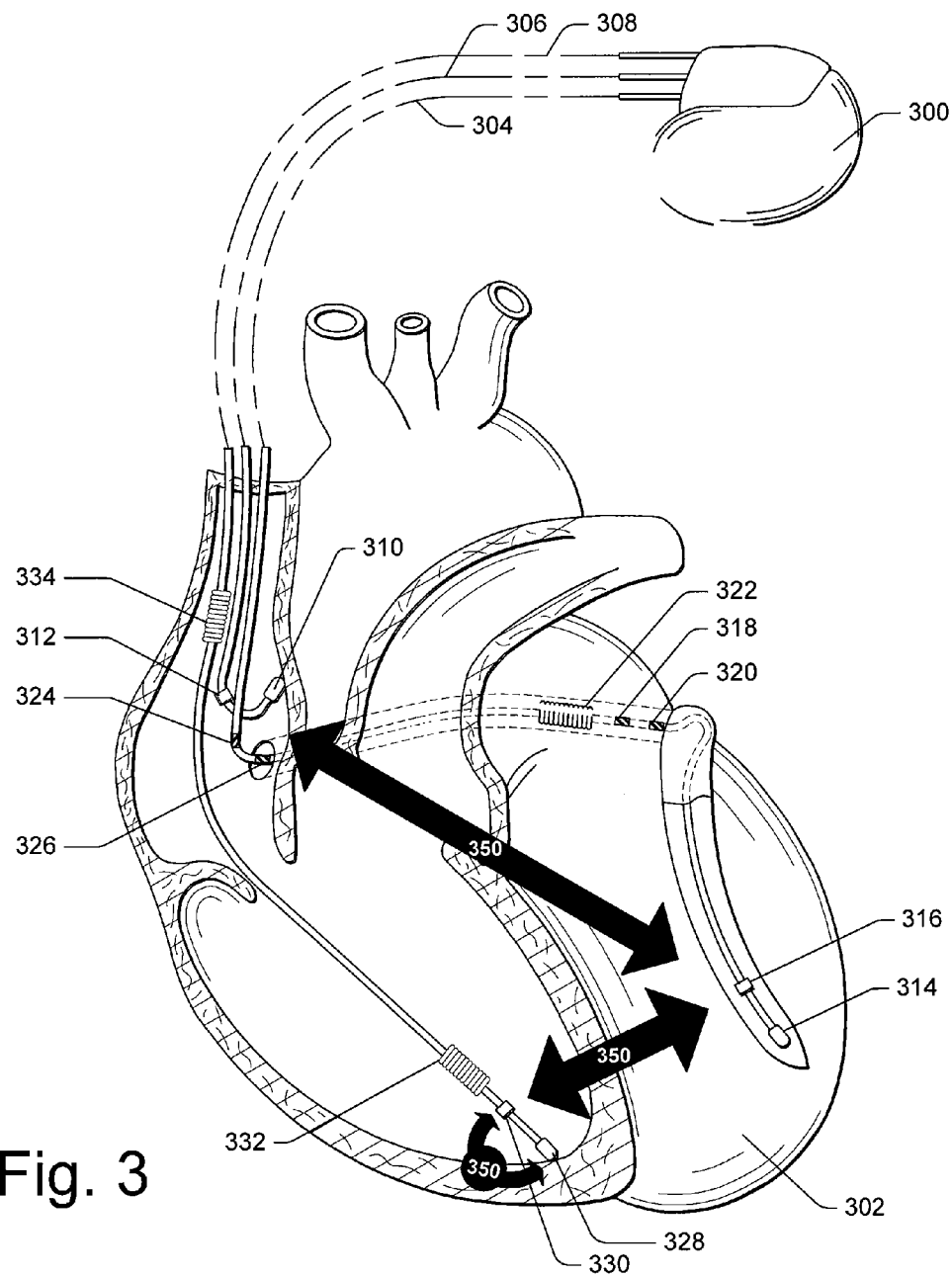
FIG. 3 is a diagram of an exemplary implantable device in relation to a human heart, including implantable lead system and multi-vector network.

As shown in FIG. 3, an exemplary implantable medical device ("implantable device" 300), in this case an exemplary implantable cardioverter-defibrillator (ICD), is in electrical communication with a patient's heart 302 by way of three leads, 304, 306 and 308, suitable for sensing, delivering multi-chamber stimulation and shock therapy. Not every configuration has all of the illustrated electrodes, but a given actual configuration may include some of the illustrated electrodes and/or even more electrodes than illustrated.

To sense atrial cardiac signals and to provide right atrial chamber stimulation therapy, the implantable device 300 is coupled to an implantable right atrial lead 306, typically having an atrial tip electrode 310 and an atrial ring electrode 312, which typically is implanted in the patient's right atrial appendage. Implantable device 300 is also known as and referred to as a pacing device, a pacing apparatus, a cardiac rhythm management device, or an implantable cardiac stimulation device. Alternatively, the implantable device 300 could be a defibrillator, or cardioverter, or have combined pacing and defibrillation/cardioversion capabilities.

To sense left atrial and ventricular cardiac signals and to provide left chamber pacing therapy, the implantable device 300 is coupled to a "coronary sinus" lead 304 designed for placement in the "coronary sinus region" via the coronary sinus opening for positioning a distal electrode adjacent to the left ventricle or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 304 is designed to receive atrial and ventricular cardiac signals and to deliver left ventricular pacing therapy using a left ventricular (LV) tip electrode 314 and a LV ring electrode 316. Left atrial pacing therapy uses, for example, first and second left atrial (LA) ring electrodes 318 and 320. Shocking therapy can be performed using at least a left atrial (LA) coil electrode 322. For a description of an exemplary coronary sinus lead, see U.S. Pre-Grant Publication No. 20030050681, "A Self-Anchoring Coronary Sinus Lead" (Pianca et al.), and U.S. Pat. No. 5,466,254 to Helland, entitled, "Coronary Sinus Lead with Atrial Sensing Capability," which patent documents are incorporated herein by reference. Coronary sinus lead 304 may also include a pair of right atrial (RA) ring electrodes 324 and 326, which may be used to provide right atrial chamber pacing therapy.

The implantable device 300 is also shown in electrical communication with the patient's heart 302 by way of an implantable right ventricular lead 308, typically having an right ventricular (RV) tip electrode 328, an RV ring electrode 330, an RV coil electrode 332, and a superior vena cava (SVC) coil electrode 334 (also known as a right atrial (RA) coil electrode). Typically, the right ventricular lead 308 is transvenously inserted into the heart 302 so as to place the right ventricular tip electrode 328 in the right ventricular apex so that the RV coil electrode 332 will be positioned in the right ventricle and the SVC coil electrode 334 will be positioned in the superior vena cava. Accordingly, the right ventricular lead 308 is capable of receiving cardiac signals, and delivering stimulation in the form of pacing and shock therapy to the right ventricle.

A multi-vector network 350 can obtain impedance measurements over multiple vectors simultaneously, quasi-simultaneously, or sequentially using any of the electrodes illustrated in FIG. 3, either in pairs or in combinations of three or more electrodes. For the sake of illustration, an exemplary multi-vector network 350 is shown in FIG. 3. Although the illustrated multi-vector network 350 includes three vectors, other exemplary multi-vector networks 350 may include more (or less) than three vectors. The illustrated multi-vector network 350 includes three intracardiac vectors: a vector between the left ventricle (LV) and the right atrium (RA), a vector between the LV and the right ventricle (RV), and a vector between two electrodes in the right ventricle (RV).

The term "multi-vector network 350" will be used herein to refer to any multi-vector network with two or more vectors between physical, logical, and or virtual electrodes, such as between the physical electrodes illustrated in FIG. 3. In the description below, "multi-vector network 350" sometimes includes at least one intracardiac vector—a vector confined to within cardiac tissue, or within the pericardial sac.

Figure 4:
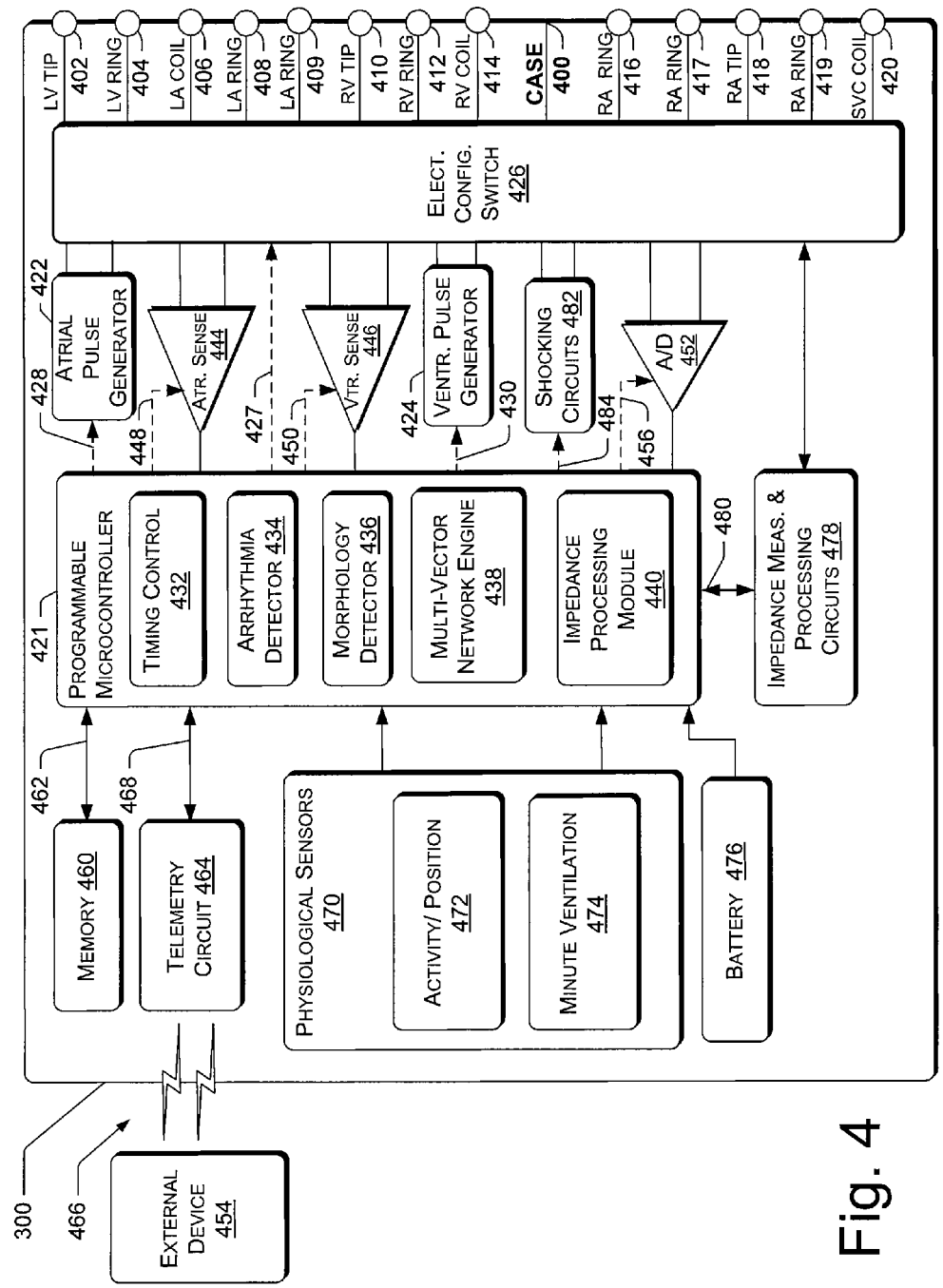
FIG. 4 is a block diagram of the exemplary implantable device of FIG. 3, in greater detail.

FIG. 4 shows an exemplary block diagram depicting various components of the exemplary implantable device 300. The components are typically contained in a case 400, which is often referred to as the "can", "housing", "encasing", or "case electrode", and may be programmably selected to act as the return electrode for unipolar operational modes. The case 400 may further be used as a return electrode alone or in combination with one or more of the coil electrodes 322, 332, 334 for stimulating purposes. The case 400 further includes a connector (not shown) having a plurality of terminals (402, 404, 406, 408, 409, 410, 412, 414, 416, 417, 418, 419, and 420—shown schematically with the names of the electrodes to which they are connected shown next to the terminals), including:

a left ventricular tip terminal (LV TIP) 402 for left ventricular tip electrode 314;

a left ventricular ring terminal (LV RING) 404 for left ventricular ring electrode 316;

a left atrial shocking terminal (LA COIL) 406 for left atrial coil electrode 322;

a left atrial ring terminal (LA RING) 408 for left atrial ring electrode 318;

a left atrial ring terminal (LA RING) 409 for left atrial ring electrode 320;

a right ventricular tip terminal (RV TIP) 410 for right ventricular tip electrode 328;

a right ventricular ring terminal (RV RING) 412 for right ventricular ring electrode 330;

a right ventricular shocking terminal (RV COIL) 414 for RV coil electrode 332;

a right atrial ring terminal (RA RING) 416 for atrial ring electrode 324;

a right atrial ring terminal (RA RING) 417 for right atrial ring electrode 326;

a right atrial tip terminal (RA TIP) 418 for atrial tip electrode 310;

a right atrial ring terminal (RA RING) 419 for atrial ring electrode 312; and a SVC shocking terminal (SVC COIL) 420 for right atrial SVC coil electrode 334.

An exemplary implantable device 300 may include a programmable microcontroller 421 that controls various operations of the implantable device 300, including cardiovascular monitoring, hemodynamic monitoring, and cardiovascular stimulation therapy. Microcontroller 421 includes a microprocessor (or equivalent control circuitry), RAM and/or ROM memory, logic and timing circuitry, state machine circuitry, and I/O circuitry.

The exemplary implantable device 300 may further include an atrial pulse generator 422 and a ventricular pulse generator 424 that generate pacing stimulation pulses for delivery by the right atrial lead 306, the coronary sinus lead 304, and/or the right ventricular lead 308 via an electrode configuration switch 426. The electrode configuration switch 426 may include multiple switches for connecting the desired electrodes to the appropriate I/O circuits, thereby providing complete electrode programmability. Accordingly, switch 426, in response to a control signal 427 from the microcontroller 421, determines the polarity of the stimulation pulses (e.g., unipolar, bipolar, etc.) by selectively closing the appropriate combination of switches.

To provide stimulation therapy in each of the four chambers of the heart, the atrial and ventricular pulse generators 422 and 424 may include dedicated, independent pulse generators, multiplexed pulse generators, or shared pulse generators. The pulse generators 422 and 424 are controlled by the microcontroller 421 via appropriate control signals 428 and 430, respectively, to trigger or inhibit the stimulation pulses.

Microcontroller 421 is illustrated as including timing control circuitry 432 to control the timing of the stimulation pulses (e.g., pacing rate, atrioventricular (AV) delay, atrial interconduction (A-A) delay, or ventricular interconduction (V-V) delay, native atrial event to native or stimulated ventricular event (PV) delay, (AV/PV) delay, etc.). The timing control circuitry may also be used for the timing of refractory periods, blanking intervals, noise detection windows, evoked response windows, alert intervals, marker channel timing, and so on.

Microcontroller 421 may also implement an arrhythmia detector 434, a morphology detector 436, a multi-vector network engine 438, and an impedance processing module 440. The microcontroller 421 may process input from physiological sensors 470, such as accelerometers of an activity/position module 472, and a minute ventilation module 474, etc., The components 434, 436, 438, and 440 may be implemented in hardware as part of the microcontroller 421, or as software/firmware instructions programmed into an implementation of the implantable device 300 and executed on the microcontroller 421 during certain modes of operation. Although not shown, the microcontroller 421 may further include other dedicated circuitry and/or firmware/software components that assist in monitoring various conditions of the patient's heart and managing pacing therapies.

Atrial sensing circuits 444 and ventricular sensing circuits 446 may also be selectively coupled to the right atrial lead 306, coronary sinus lead 304, and the right ventricular lead 308, through the switch 426 to detect the presence of cardiac activity in each of the four chambers of the heart. The sensing circuits 444 and 446 may include dedicated sense amplifiers, multiplexed amplifiers, or shared amplifiers. Switch 426 determines the "sensing polarity" of the cardiac signal by selectively closing the appropriate switches. In this way, the clinician may program the sensing polarity independent of the stimulation polarity.

Each sensing circuit 444 and 446 may employ one or more low power precision amplifiers with programmable gain and/or automatic gain control, bandpass filtering, and a threshold detection circuit to selectively sense the cardiac signal of interest. The automatic gain control enables the exemplary implantable device 300 to sense low amplitude signal characteristics of atrial or ventricular fibrillation.

The outputs of the atrial and ventricular sensing circuits 444 and 446 are connected to the microcontroller 421 which, in turn, is able to trigger or inhibit the atrial and ventricular pulse generators 422 and 424 in a demand fashion in response to the absence or presence of cardiac activity in the appropriate chambers of the heart. The sensing circuits 444 and 446 receive control signals from the microcontroller 421 over signal lines 448 and 450 to control, for example, the gain and the timing of blocking circuitry (not shown) optionally coupled to the inputs of the sensing circuits 444, 446.

Cardiac signals, including signals involved in impedance measurements, are supplied to an analog-to-digital (A/D) data acquisition system 452, which is configured to acquire these signals, convert the raw analog data into a digital signal, and store the digital signals for later processing and/or telemetric transmission to an external device 454. The data acquisition system 452 is coupled to the right atrial lead 306, the coronary sinus lead 304, and the right ventricular lead 308 through the switch 426 to process signals across any pair of desired electrodes.

The data acquisition system 452 is coupled to the microcontroller 421, or other detection circuitry, to assist in detecting an evoked response from the heart 302 in response to an applied stimulus, which is often referred to as detecting "capture". Capture occurs when an electrical stimulus applied to the heart is of sufficient energy to depolarize the cardiac tissue, thereby causing the heart muscle to contract. The microcontroller 421 detects a depolarization signal during a window following a stimulation pulse, the presence of which indicates that capture has occurred. The microcontroller 421 enables capture detection by triggering the ventricular pulse generator 424 to generate a stimulation pulse, starting a capture detection window using the timing control circuitry 432 within the microcontroller 421, and enabling the data acquisition system 452 via control signal 456 to sample the cardiac signal that falls in the capture detection window and, based on the amplitude, determines if capture has occurred.

The microcontroller 421 is further coupled to a memory 460 by a suitable data/address bus 462. The programmable operating parameters used by the microcontroller 421 are stored in memory 460 and used to customize the operation of the exemplary implantable device 300 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart 302 within each respective tier of therapy.

The operating parameters of the exemplary implantable device 300 may be non-invasively programmed into the memory 460 through a telemetry circuit 464 in telemetric communication via communication link 466 with the external device 454, such as a programmer, local transceiver, or a diagnostic system analyzer. The microcontroller 421 can activate the telemetry circuit 464 with a control signal 468. The telemetry circuit 464 allows intracardiac electrograms and status information relating to the operation of the exemplary implantable device 300 (as contained in the microcontroller 421 or memory 460) to be sent to the external device 454 through an established communication link 466.

The physiological sensors 470 referred to above can further include, for example, "rate-responsive" sensors that adjust pacing stimulation rates according to the exercise state of the patient. Accordingly, the microcontroller 421 responds by adjusting the various pacing parameters (such as rate, etc.) at which the atrial and ventricular pulse generators 422 and 424 generate stimulation pulses.

The physiological sensors 470 may include mechanisms and sensors to detect bodily movement (472), minute ventilation 474, changes in blood pressure, changes in cardiac output, changes in the physiological condition of the heart, diurnal changes in activity (e.g., detecting sleep and wake states), G-force acceleration of the ICD case 400, length of the cardiac QT interval, blood oxygen saturation, blood pH, changes in temperature, respiration rate, and QRS wave duration. While shown as being included within the exemplary implantable device 300, the physiological sensor(s) 470 may also be external to the exemplary implantable device 300, yet still be implanted within or carried by the patient, e.g., a blood pressure probe. Examples of physiological sensors external to the case 400 that may be deployed by implantable device 300 include sensors that, for example, sense respiration activities, $O_2$ saturation, evoked response, pH of blood, and so forth.

The illustrated physiological sensors 470 include one or more activity/position sensors 472 (e.g., 1D or 3D accelerometers, movement sensors, etc.) to detect changes in the patient's position. The activity/position sensors 472 can be used to assist detection of orthostatic hypotension caused by transition from a less upright posture to a comparatively more upright posture. One example postural change leading to orthostatic hypotension in susceptible individuals is a movement from a supine position in a rest state (e.g., sleeping in bed) to an upright position in a non-rest state (e.g., sitting or standing up).

In one configuration, accelerometer output signal is bandpass-filtered, rectified, and integrated at regular timed intervals. A processed accelerometer signal can be used as a raw activity signal. The device derives an activity measurement based on the raw activity signal at intervals timed according to the cardiac cycle. The activity signal alone can be used to indicate whether a patient is active or resting. The activity measurement can further be used to determine an activity variance parameter. A large activity variance signal is indicative of a prolonged exercise state. Low activity and activity variance signals are indicative of a prolonged resting or inactivity state.

The minute ventilation (MV) sensor 474 may also be included in the physiological sensors 470 in order to sense rate and depth of breathing. Minute ventilation can be measured as the total volume of air that moves in and out of a patient's lungs in a minute. The MV sensor 474 may use impedance measuring and processing circuits 478 to sense air movement by measuring impedance across the chest cavity.

The impedance measuring and processing circuits 478 communicate with the microcontroller 421, e.g., via control signals 480 and can be used for obtaining many types of bodily and intracardiac impedances, including a network of single- or multi-vector impedance measurements. Such impedance measurements can be used for trending many kinds of physiological variables, and can also be used for detection of air movement in and out of the lungs, blockage of airways, lead impedance surveillance during acute and chronic phases for proper lead positioning or dislodgement; lead integrity by detecting insulation abrasion, operable electrodes, and automatically switching to an operable pair if dislodgement occurs; measuring respiration or minute ventilation; measuring thoracic impedance for determining shock thresholds; detecting when the device has been implanted; measuring cardiac stroke volume; detecting the opening of heart valves; and so forth. The impedance measuring circuit 478 may be coupled to the switch 426 so that any desired electrode may be used, and networks of vectors can be selected by the multi-vector network engine 438.

The exemplary implantable device 300 additionally includes a battery 476 that provides operating power to all of the components shown in FIG. 4. The battery 476 is capable of operating at low current drains for long periods of time (e.g., less than 10 μA), and is capable of providing high-current pulses (for capacitor charging) when the patient requires a shock pulse (e.g., in excess of 10 A, at voltages above 500 V, for periods of 2-20 microseconds). The battery 476 also desirably has predictable discharge characteristics so that elective replacement time can be detected. As one example, the exemplary implantable device 300 employs lithium/silver vanadium oxide batteries.

The exemplary implantable device 300 can further include magnet detection circuitry (not shown), coupled to the microcontroller 421, to detect when a magnet is placed over the exemplary implantable device 300. A magnet may be used by a clinician to perform various test functions of the exemplary implantable device 300 and/or to signal the microcontroller 421 that an external programmer (e.g., 454) is in place to receive or transmit data to the microcontroller 421 through the telemetry circuits 464.

The microcontroller 421 further controls a shocking circuit 482 via a control signal 484. The shocking circuit 482 generates shocking pulses of low (e.g., up to 0.5 joules), moderate (e.g., 0.5-10 joules), or high energy (e.g., 11-40 joules), as selected by the microcontroller 421. Such shocking pulses are applied to the patient's heart 302 through at least two shocking electrodes selected, for example, from the left atrial coil electrode 322, the RV coil electrode 332, and/or the SVC coil electrode 334. As noted above, the case 400 may act as an active electrode in combination with the RV coil electrode 332, or as part of a split electrical vector using the SVC coil electrode 334 or the left atrial coil electrode 322 (i.e., using the RV coil electrode 332 as a common electrode).

Cardioversion shocks are generally considered to be of low to moderate energy level (so as to minimize pain felt by the patient), and/or synchronized with an R-wave and pertain to the treatment of tachycardia. Defibrillation shocks are generally of moderate to high energy level (i.e., corresponding to thresholds in the range of, e.g., 5-40 joules), delivered asynchronously (since R-waves may be too disorganized), and pertain exclusively to the treatment of fibrillation. Accordingly, the microcontroller 421 is capable of controlling the synchronous or asynchronous delivery of the shocking pulses.

More generally, the exemplary implantable device 300 can be programmed to stimulate different sets of vascular and cardiac muscles through the same lead/electrode system. The exemplary implantable device 300 can be programmed to vary the output voltage of various pulses to effectively stimulate different muscles of the heart and blood vessels, even though the physical placement of leads and electrodes does not change.

Exemplary Waveform Generating and Impedance Measuring Architecture

Figure 5:
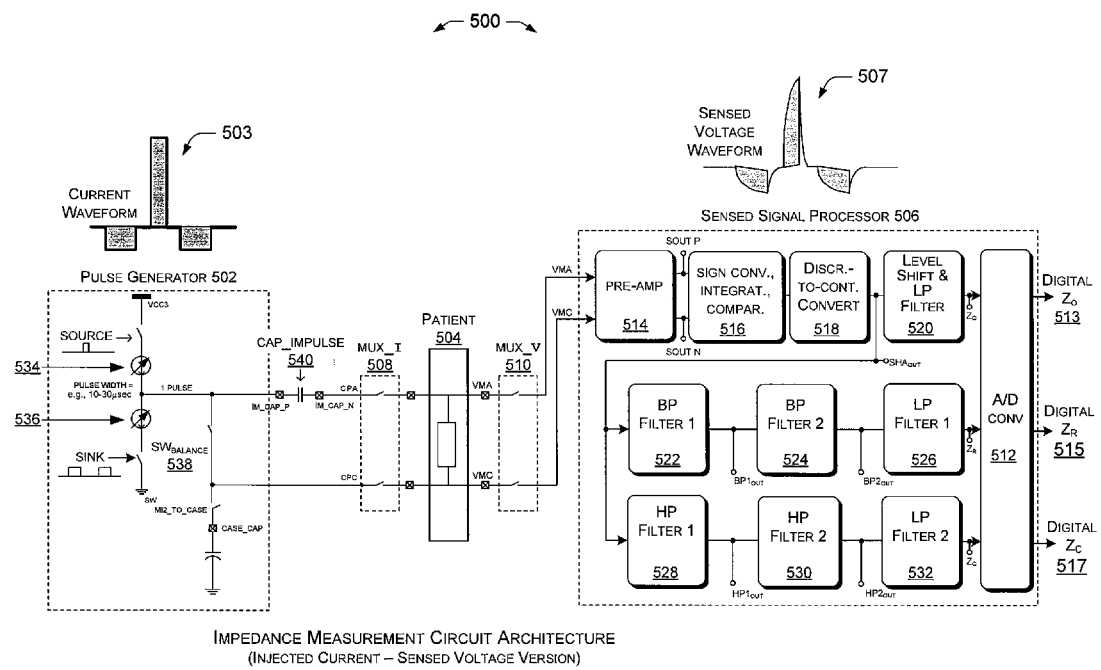
FIG. 5 is a block diagram of an exemplary impedance measurement circuit architecture.

FIG. 5 shows an exemplary impedance measurement circuit architecture 500, including filter components to obtain raw, cardiac, and respiratory impedances. The illustrated architecture 500 is just one example configuration, other configurations are also possible. In one implementation, the exemplary impedance measurement architecture 500 includes a pulse generator 502 for generating an exemplary pulse waveform, in this case a current waveform 503, for application to the bodily tissue of a patient 504 and a sensed signal processor 506 for processing resulting waveforms detected in the tissue, in this case voltage waveforms 507. An injection (e.g., current pulse) multiplexor 508 implements the single- or multi-vector aspect of signal application by determining a first set of electrodes for injecting the exemplary waveform 503. The selection of electrodes may be determined by the network specifier 602 of the multi-vector network engine 438. Likewise, a sensing (voltage measurement) multiplexer 510 implements signal sensing by determining a second set of electrodes for sensing the resulting voltage waveforms 507. The set of sensing electrodes may also be determined by the network specifier 602 of the multi-vector network engine 438. Both the injection multiplexor 508 and the sensing multiplexor 510 may be implemented in an implantable device 300 in the electrode configuration switch 426.

Exemplary Probative Waveform

A waveform 503 for application to bodily tissue that is generated by the exemplary impedance measurement circuit architecture 500 possesses many special waveform features and electrical characteristics that are well suited for probing and measuring many types of physiological parameters in the body using current modulated or voltage modulated pulses. Such waveforms are described, as introduced above, in U.S. Patent Application No. 60/787,884 to Wong et al, entitled "Tissue Characterization Using Intracardiac Impedances with an Implantable Lead System," filed Mar. 31, 2006, and incorporated herein by reference in its entirety. Exemplary waveforms 503 are multi-phasic, with negative phases (pulse segments below baseline) that balance positive phases (pulse segments above baseline). The illustrated waveform 503 is tri-phasic. Other versions of the waveform 503 may have more than three phases, may be synchronous or asynchronous, may be rectangular or sinusoidal, etc. One version of the waveform 503 uses the sinc(x) sampling waveform. In one variation, the exemplary impedance measurement architecture applies the waveform 503 as a voltage waveform instead of a current waveform and senses the results as electrical current instead of voltage.

Properties of the exemplary waveforms 503 include superior penetration of some tissues than conventionally injected signals; better differential penetration of tissues than conventionally injected signals for improved differentiation and characterization of tissues; broader frequency spectrum content than conventionally injected signals in order to characterize tissue; greater neutrality in the body than conventionally injected signals, i.e., the exemplary waveforms do not change the parameter they are trying to measure, and moreover, do not create ionic imbalances or imbalances of charge, voltage, etc., in the tissues or at tissue-electrode interfaces.

Each waveform 503 has a total duration less than the charging time constant of the electrode-electrolyte interfaces used to inject and sense the signals. These time constants are typically in the range of a few milliseconds. In one implementation, the duration of waveform 503 is less than 1 millisecond. This waveform feature is helpful for minimizing polarization effects at these electrode-electrolyte interfaces. Other features of the exemplary waveforms 503 include symmetric or asymmetric phase duration, decreasing phase amplitudes, and alternating phase signs. Each waveform 503 typically has null durations in between phases to provide time to allow complete processing of information caused by one phase before the next phase of the waveform 503 begins. Implementations of the waveform 503 that have near perfect square wave pulses (or rectangular wave pulses) contain a great deal of high-frequency content. Near-sinusoidal implementations of the waveform 503 may contain less high frequency content than the rectangular wave versions.

The features of exemplary waveforms 503 just enumerated provide numerous advantages, including: eliminating the need for fast digital sampling, minimizing artifacts introduced in the measurement process, increased tolerance of small phase delays between injected and sensed signals. The exemplary waveforms 503 also lend themselves to CMOS realization using low-value switched capacitor solutions. Further, the wide frequency spectrum of the injected signal can be used to implement algorithms that differentiate tissues based on their frequency response, and/or phase delay. The very low duty-cycle of the exemplary waveforms 503 make them safer for patients. The reduced duty-cycle brings the injected charge and the root-mean-square value of the injected signal well below levels that could be perceived by the patient or that could induce adverse events.

It is important to note that the net-zero voltage feature, also referred to as the voltage-balanced feature, refers to the voltage formed on blocking capacitors that appear in series with the load. The flow of current through these capacitors builds up voltage across them. Since these capacitors, such as capacitor 540 in FIG. 5, also appear in circuits that are responsible for sensing cardiac activity, it is important that the net voltage built up on them be zero. As a result of the net-zero voltage feature, the influence of an exemplary waveform 503 on the circuits that sense cardiac activity is minimal.

Other features of the exemplary waveforms 503 derive from the above-mentioned null segments—intra-waveform segments containing no signal—that serve several purposes. First, the null segments allow the electronics in processing circuits to settle during measurement of phases and second, they allow multiple instances of the waveform 503 to exist in the patient's tissue simultaneously, being staggered by time multiplexing such that a phase of one waveform can be measured during the time that there is no signal between phases of another waveform.

In one implementation, the exemplary waveform 503 is used to derive physiological measurements based on intracardiac impedances. Based on such cardiogenic impedance measurements, many physiological variables can be trended to detect changes in a patient's condition, such as congestive heart failure (CHF) index, pulmonary edema, systolic slope, contraction (e.g., dZ/dt(max)), diastolic slope, relaxation (e.g., dZ/dt(min)), pre-ejection period (in low resolution), ejection time, left ventricular ejection fraction (LVEF), diastolic heart failure index (DHFI), cardiac index, etc.

The exemplary waveform 503 provides an elegant and reliable vehicle for measuring bodily impedances in a manner that gives reliably reproducible results. Instead of a conventional technique of trying to sense an instantaneous "snapshot" measurement of a conventionally injected signal, the impedance measurement circuit architecture 500 derives an impedance measurement by dividing the area under the sensed voltage curve (waveform 507) by the area of the injected current waveform 503. An exemplary implantable device 300 can perform this exemplary method by "integrating the curve" of an absolute value of waveforms 503 or 507. Sometimes the exemplary implantable device can closely approximate this integration without having to perform an integration operation by directly measuring and summing the area "under" the curve (e.g., under the rectangular wave) of the waveform 503, that is, the area composed of the absolute value of the three areas of the three phases of an exemplary tri-phasic waveform 503.

Likewise, the exemplary implantable device can integrate, or closely approximate the integration, by measuring and summing the area "under" the curve (e.g., the rectangular wave) of the waveform 507, that is, the area composed of the absolute value of the three areas of the three phases. In one implementation, the area of the sensed voltage, waveform 507, is measured at the output of an integrator circuit. The area of the injected current, waveform 503, is computed by, or preset by, the micro-controller driving the implantable device. An implantable device 300 may thus use this area-based ("areal") approach to deriving a network of impedance measurements over a multi-vector network 350.

Exemplary Sensing Circuitry Architecture

Returning to description of the impedance measurement circuit architecture 500 itself, the sensed signal processor 506 typically consists of pre-amplification circuitry, switched capacitor filters, and an analog to digital converter 512. In one implementation, the voltage signal from the voltage measurement multiplexer 510 is processed by several voltage measurement lines or paths. The illustrated sensed signal processor 506 is able to obtain at least the three different impedance signals introduced above with respect to FIG. 5, that is, low frequency raw impedance $Z_o$ 513, respiration impedance $Z_r$ 515, and cardiac impedance $Z_c$ 517. Each measurement can be activated separately or simultaneously.

A digital form of raw impedance $Z_o$ 513 may be obtained. First, the sensed signal, i.e., the tri-phasic voltage waveform 507 from the voltage measurement multiplexer 510, is sent to a preamplifier 514. The next stage is embodied in a sign conversion and integration module 516. At this stage, the signal is converted into an absolute value and then integrated over time. Using the integration process instead of conventional instantaneous "snapshot" measurements of impedance components such as pure resistance produces results that are more noise-free and more accurate than the conventional techniques.

The signal is then applied to a discrete-to-continuous signal conversion module 518. At this point in the architecture 500, the signals for low frequency impedance $Z_o$ 513, respiration impedance $Z_r$ 515, and cardiac impedance $Z_c$ 517 are extracted separately by different filter paths, as summarized in FIG. 5. To obtain the low frequency impedance $Z_o$ 513, the signal is sent to a level shift and low pass filter module 520, and then to the analog to digital converter 512.

A digital form of the respiration impedance $Z_r$ 515 may be obtained by tapping the analog signal from the input of the level shift and low pass filter module 520, and feeding the signal to a line consisting of bandpass filters 522 and 524 and a low pass filter 526. The signal is then fed to the analog to digital converter 512 to obtain digital $Z_r$ 515.

A digital form of the cardiac impedance $Z_c$ 517 may likewise be obtained by tapping the analog signal from the input of the level shift and low pass filter module 520, and feeding the signal to a line consisting of high pass filters 528 and 530 and a low pass filter 532. The signal is then fed to the analog to digital converter 512 to obtain digital $Z_c$ 517.

In one implementation, the pulse generator 502 consists of two timing-controlled current generators 534 and 536 with programmable magnitude. The first current generator 534 sources current, the other current generator 536 sinks the current. As part of the charge and voltage balancing process, the switch $SW_{Balance}$ 538 is used to discharge the external capacitor Cap_Impulse 540 after each generated impulse. The pulse rate is programmable.

Components of the impedance measurement architecture 500 may be distributed across the impedance measuring & processing circuits 478 (FIG. 4) and the impedance processing module 440 (FIG. 4), the distribution of components depending on implementation. That is, the exemplary impedance measurement architecture 500 may be implemented in hardware, software, or combinations thereof. For example, the exemplary impedance measurement architecture 500 may be implemented in hardware as part of the microcontroller 421 and/or as hardware integrated into the fabric of the exemplary implantable device 300; or as software/firmware instructions programmed into an implementation of the implantable device 300 and executed on the microcontroller 421 during certain modes of operation.

In one implementation, the preamplifier 514 is included in the impedance measuring & processing circuits 478. The pulse generator 502 can be implemented in the impedance processing module 440 as may some of the other components of the sensed signal processor 506.

Although the illustrated version of the impedance measurement circuit architecture 500 applies a current pulse waveform 503 and senses a voltage pulse waveform 507, other implementations can inject a voltage waveform and sense a current waveform.

The "raw" impedance measurement, $Z_o$ 513, can be useful for determining extra- or intra-cardiac impedances and examining conditions such as pulmonary edema. The respiration component of impedance, $Z_r$ 515, can be useful for tracking respiration rate and depth, sleep apnea, and other related CHF conditions. Likewise, the cardiac component of impedance, $Z_c$ 517, can be separated out for tracking various hemodynamic parameters.

Exemplary Multi-Vector Network Engine

Figure 6:
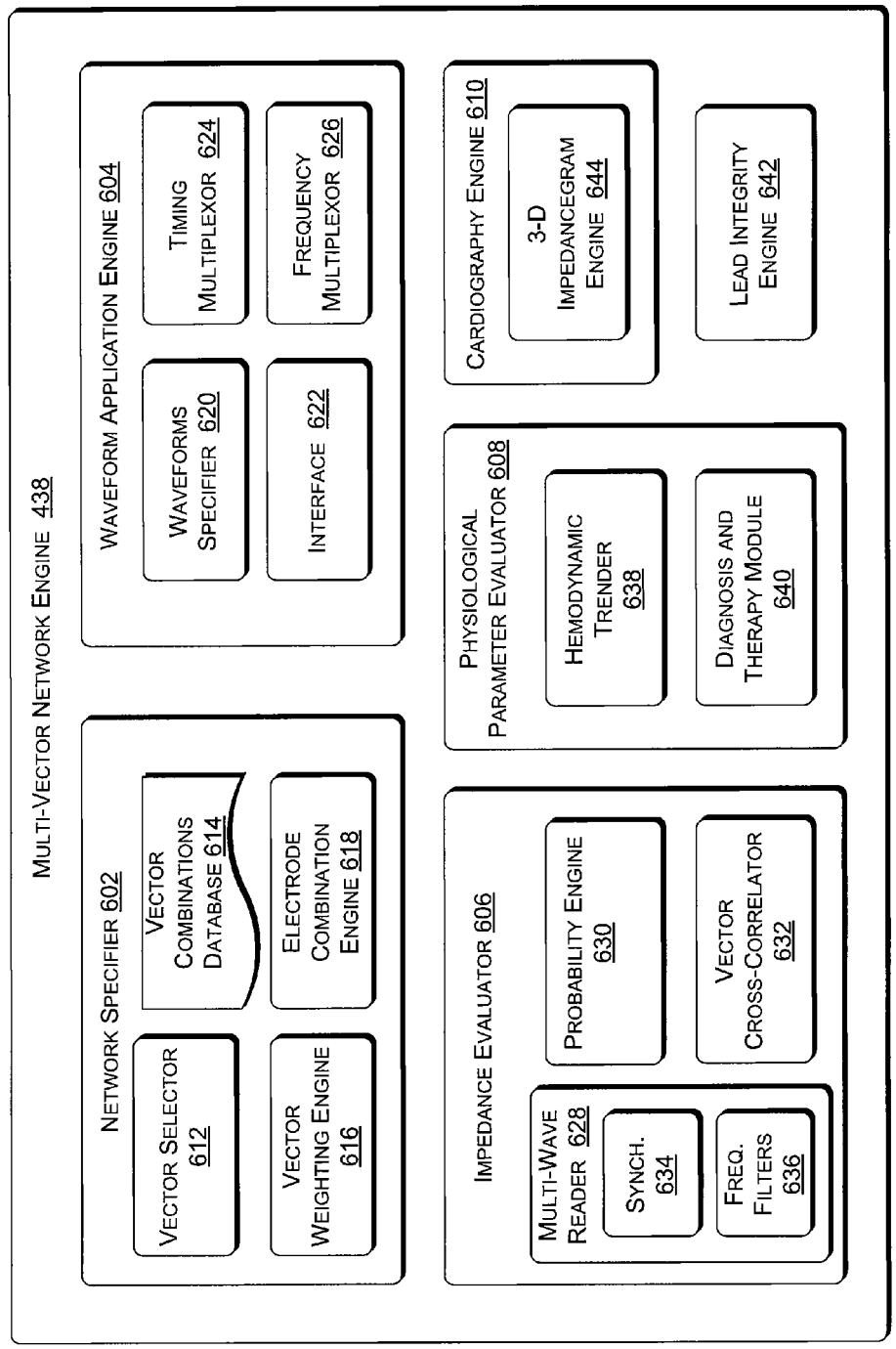
FIG. 6 is a block diagram of an exemplary multi-vector network engine.

FIG. 6 shows the exemplary multi-vector network engine 438 of FIG. 4 in greater detail. The illustrated configuration of the exemplary multi-vector network engine 438 is meant to provide one example configuration for the sake of overview. Many other configurations of the illustrated components, or similar components, are possible within the scope of the subject matter. Such a multi-vector network engine 438 can be executed in hardware, software, or combinations of hardware, software, firmware, etc. In some implementations, the multi-vector network engine 438 is integrated with the impedance measurement circuit architecture 500, while in other versions the multi-vector network engine 438 comprises mostly software that communicates with the impedance measurement circuit architecture 500.

In one implementation, as illustrated, the exemplary multi-vector network engine 438 includes a network specifier 602, a waveform application engine 604, an electrical characteristics evaluator, such as the illustrated impedance evaluator 606, a physiological parameter evaluator 608, and a cardiography engine 610. Not all implementations will include all these components, or, these components may be combined differently or have subcomponents that are grouped differently.

The network specifier 602 may further include a vector selector 612 to select which available vectors are to be included in a given multi-vector network 350 configuration, a vector combinations database 614 to store predefined multi-vector configurations, a vector weighting engine 616 to assign an importance to each vector that is used in a given multi-vector configuration, and an electrode combination engine 618 to assign physical electrodes to theoretical multi-vector combinations.

The network specifier 602, may choose certain electrodes over others for a given multi-vector configuration in order to select a geometric shape for the vectors to describe through a tissue. That is, by selectively including electrodes in a given multi-vector network configuration, the network specifier 602 may select the shape of a volume of tissue through which vectors pass, thereby adding specificity of location to the sensed impedance effects. This ability to select a "shape" described by the electrical pathways of a multi-vector network is useful when the implanted device is to confine the sensing of impedance effects to one specific section of tissue, for example, to one chamber or to one half of the heart. The network specifier 602 selects electrodes that create vectors across the section of interest.

The waveform application engine 604 may further include a waveforms specifier 620 to request (or in some implementations to generate) waveforms at particular frequencies or timing sequences for the vectors of a given multi-vector configuration; an interface 622 (in some implementations) to communicate with the pulse generator 502; a timing multiplexor 624 (in some implementations) to control the timing that is used to apply the multiple waveforms in sequence over the multiple vectors; and in some implementations, a frequency multiplexor 626 instead of the timing multiplexor 624 in order to apply the multiple waveforms over the multiple vectors at different frequencies, one frequency per vector.

An electrical characteristics evaluator, such as the illustrated impedance evaluator 606, may include a multi-wave reader 628, a probability engine 630, and a vector cross-correlator 632. The multi-wave reader 628 may include a counterpart of the timing multiplexor 624, referred to as a synchronizer ("synch") 634, that controls timing for sensing multiple waveforms applied in sequence by the timing multiplexor 624. The multi-wave reader 628 may also include frequency filters 636 to delineate waveforms of different frequency that exist simultaneously in the patient's tissue, having been applied one frequency per vector by the waveform application engine 604.

The probability engine 630 processes the measured electrical characteristic (such as impedance) of each vector in a multi-vector configuration and may apply statistical analysis to decide how to interpret the data. For example, if the impedances of a majority set of vectors in a multi-vector network 350 trend in the same manner, but the impedance of one vector in the minority deviates notably from the majority, then the probability engine 630 may discard the deviant vector as erroneous. The probability engine 630 may also determine that a trend, such as a trend indicative of a degree of heart failure, is accelerating.

The vector cross-correlator 632 works closely with the probability engine 630 and with the physiological parameter evaluator 608 to interpret electrical results in terms of a patient's physical conditions. For example, the vector cross-correlator 632 may compare the data returned from the multiple vectors either as raw impedance data or as hemodynamic data. In other words, the same data can have more than one level of meaning, and statistical and/or cross-correlative techniques can be applied to the data in terms of these different levels—the same data can be viewed as an impedance, or as a measurement of a hemodynamic parameter, or as an indicator of a cardiac condition, such as heart failure. In one implementation, the hemodynamic trender 638 views a progression of impedance data points over time as an indicator of a cardiac condition. That is, the data points represent impedance or represent a hemodynamic parameter, while the trend itself represents an aspect of cardiac health.

In some cases, the values returned from the multiple vectors may cross-correlate to reinforce each other, serving to "double-check" the correctness of values for the parameter being measured. In other cases, some of the multiple values may give rise to additional values, that is, some of the multiple vectors may return unique information that is additive or complementary. In some cases, the vector cross-correlator 632 may subject such values to a cross-correlation algorithm based on a physiological parameter. For example, one vector may be relevant for measuring a structural change in a heart chamber, while another vector may be relevant for measuring a change in a related chamber pressure. A sample algorithm might calculate and conclude that if the change in the structure exceeds a first threshold the change in chamber pressure exceeds a second threshold, then cardiac condition "X" must be present.

Obtaining and cross-correlating data from multiple vectors at once can provide added reliability when the results of multiple vectors agree with each other, and can provide extra safeguards when the results of the multiple vectors disagree. In addition, such simultaneous or quasi-simultaneous measurements can be used to filter out noise and the presence of non-target physiological phenomena that may be affecting the target phenomena.

The diagnosis and therapy module 640 receives evaluation of the cross-correlated vectors and may make an automatic diagnosis based on the evaluation, e.g., by comparing the received values with stored thresholds. Likewise, if an implantable device diagnoses a reportable condition, then the diagnosis and therapy module 640 may signal the patient or the practitioner, depending on urgency.

Some implementations of the multi-vector network engine 438, such as that illustrated, may include a lead integrity engine 642 as well as a cardiography engine 610, which may further include a 3-D impedancegram engine 644.

It is important to note that the engines and evaluators described above could reside inside the implanted device, in an external processing unit, such as a programmer, a house-call device or a bedside monitor, or distributed between the implanted device and one or more of these external devices.

Multiplexing Measurements Over Multiple Vectors

Figure 7:
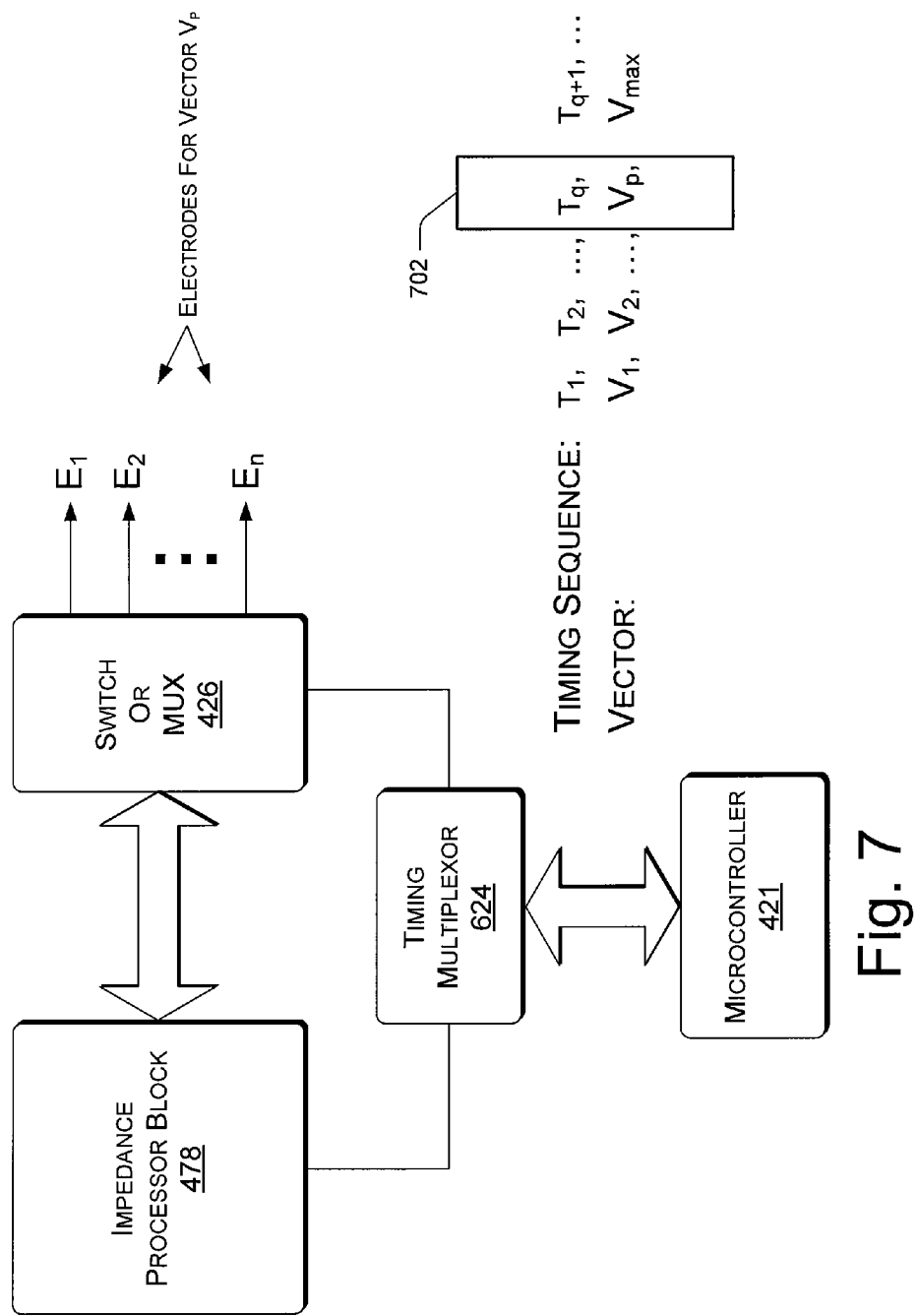
FIG. 7 is a block diagram of exemplary components for time-multiplexing signals over multiple vectors.

FIG. 7 shows a general schematic of exemplary components for applying time multiplexing. In one implementation, the timing multiplexor 624 of the waveform application engine 604 is a timing block communicatively coupled with an impedance processor block, such as impedance measuring and processing circuits 478, which may also include the pulse generator 502 and the sensed signal processor 506. The timing multiplexor 624 is coupled in turn with the microcontroller 421, which may also include elements of the pulse generator 502 and the sensed signal processor 506. Finally, the timing multiplexor 624 is coupled with the electrode configuration switch 426 or, coupled with mux 508 and mux 510.

In one implementation, the multi-vector network engine 438 residing in the microcontroller 421, programs specific timing sequences into the timing multiplexor 624. The timing sequence associates a group of electrodes that implement a given vector with the same timing point on the sequence, that is, the timing multiplexor 624 associates each vector with a point on the timing sequence 702. The electrodes associated with each vector are brought into play at the timing point of their respective vector.

Figure 8:
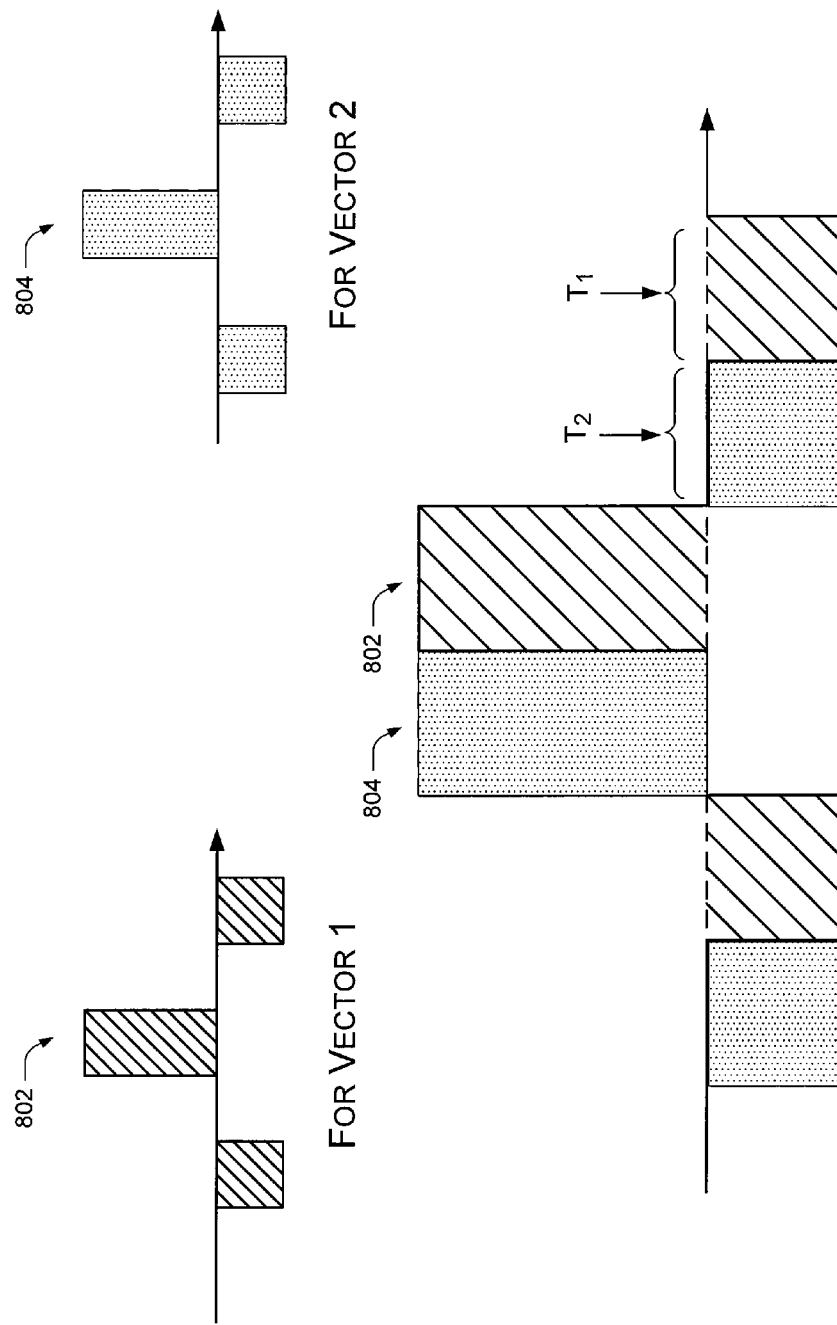
FIG. 8 is a diagram of two time-multiplexed instances of an exemplary waveform.

FIG. 8 shows the time multiplexing of two exemplary waveforms 802 and 804 by the components of FIG. 7. The first waveform 802 is used to implement a first vector $V_1$ while the second waveform 804 is used to implement a second vector $V_2$. The phases of each waveform exist in the bodily tissue at different times. Hence, for example, in the illustrated simple two vector system, at time period $T_1$ the sensed signal processor 506 can sense the first phase of the first waveform 802 for vector $V_1$ without receiving interference from the second waveform 804. At time period $T_2$ the sensed signal processor 506 can sense the first phase of the second waveform 804 for vector $V_2$ without receiving interference from the first waveform 802.

Figure 9:
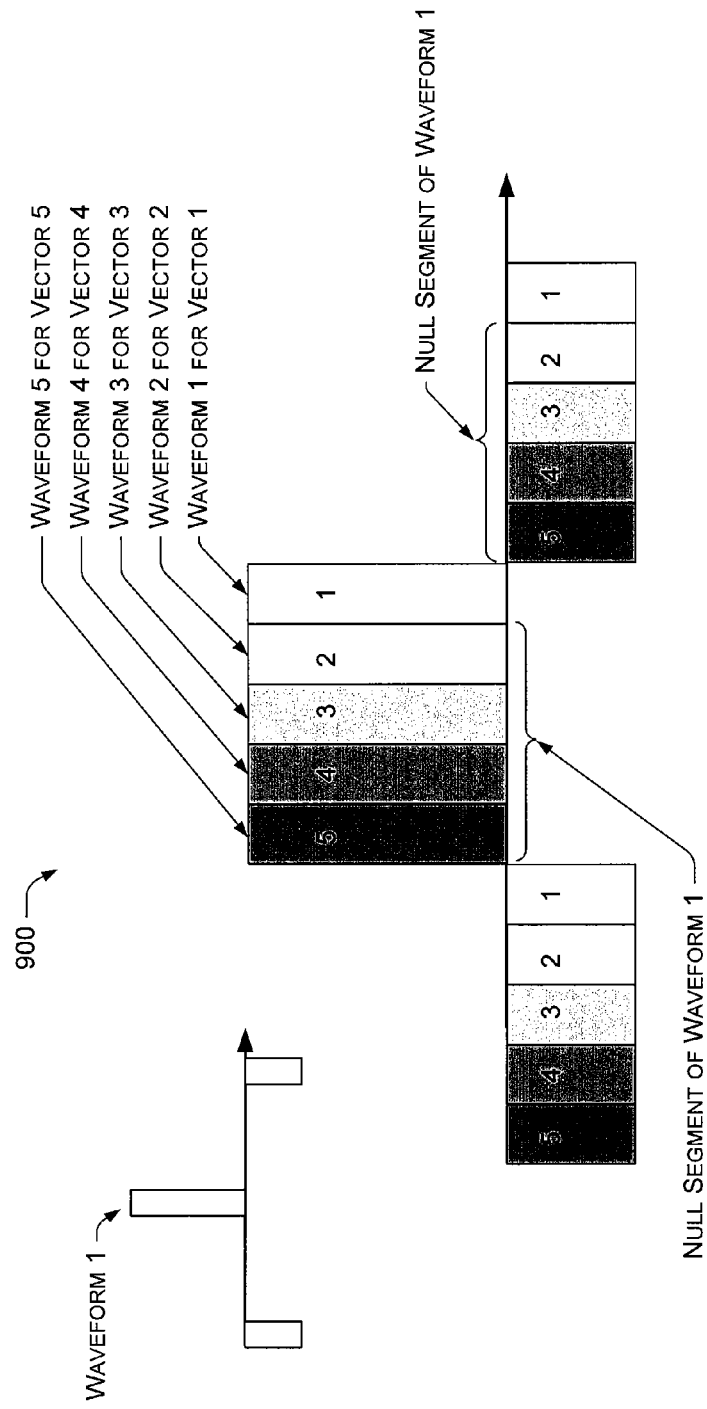
FIG. 9 is a diagram of five time-multiplexed instances of an exemplary waveform.

As shown in FIG. 9, multiple instances 900 of the exemplary waveforms, such as waveform 503, can be time-multiplexed for multiple vectors. In one implementation, the multiple instances of the multiple waveforms exist in the patient's tissue simultaneously. To use multiple instances of waveform 503, the phases of each waveform can be made of shorter duration, and the null spaces between phases can be lengthened to accommodate phases of multiple simultaneous instances of the waveform 503.

Figure 10:
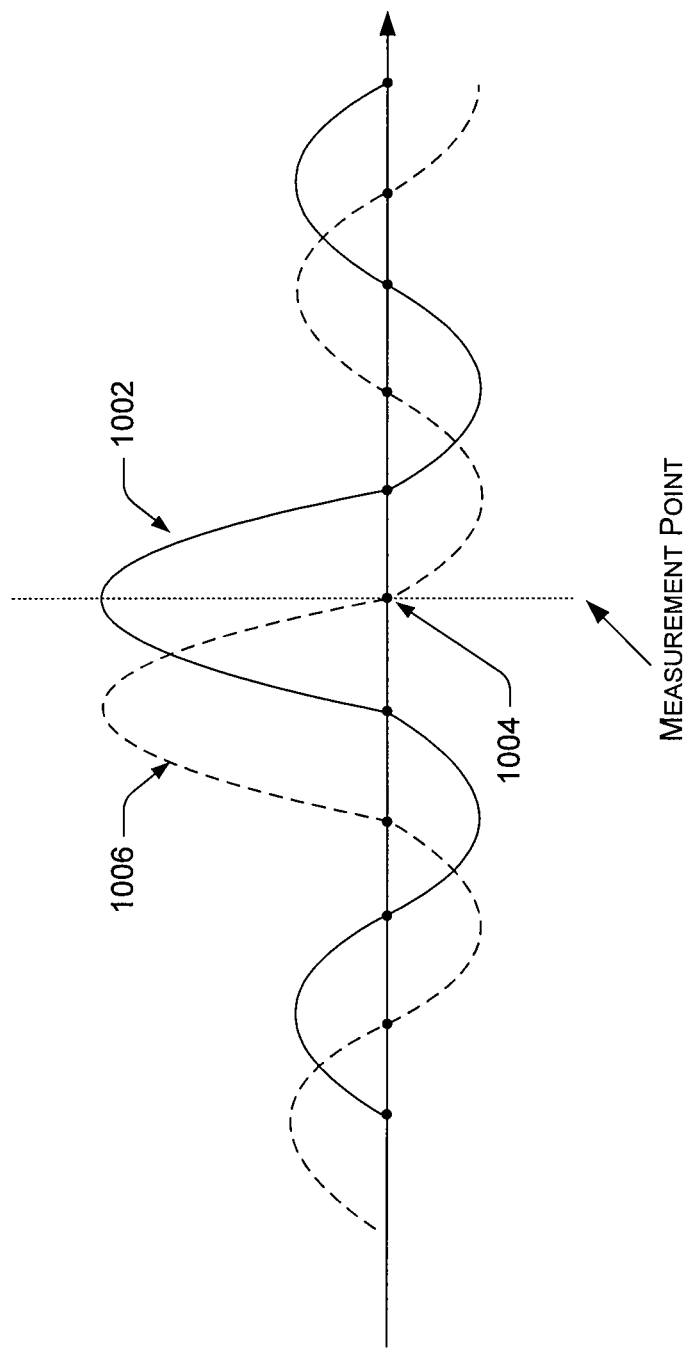
FIG. 10 is a diagram of two time-multiplexed instances of an exemplary sinc(x) waveform.

FIG. 10 shows a sinc waveform 1002, that is, sinc(x) or sin(x)/(x), used as the exemplary waveforms for determining an impedance of a bodily tissue over multiple vectors. The sinc waveform 1002 can be time-multiplexed by the arrangement of components in FIG. 7 in a like manner as the rectangular waveform 503. Instead of making measurements during the null periods of the rectangular waveforms 503, a version of the sensed signal processor 506 centers a measurement for one instance of the sinc waveform 1002 with the zero-crossing point 1004 of a second instance of the sinc(x) waveform 1006, as shown. The number of instances that can be multiplexed is determined by the configuration of the sinc waveform 1002.

Figure 11:
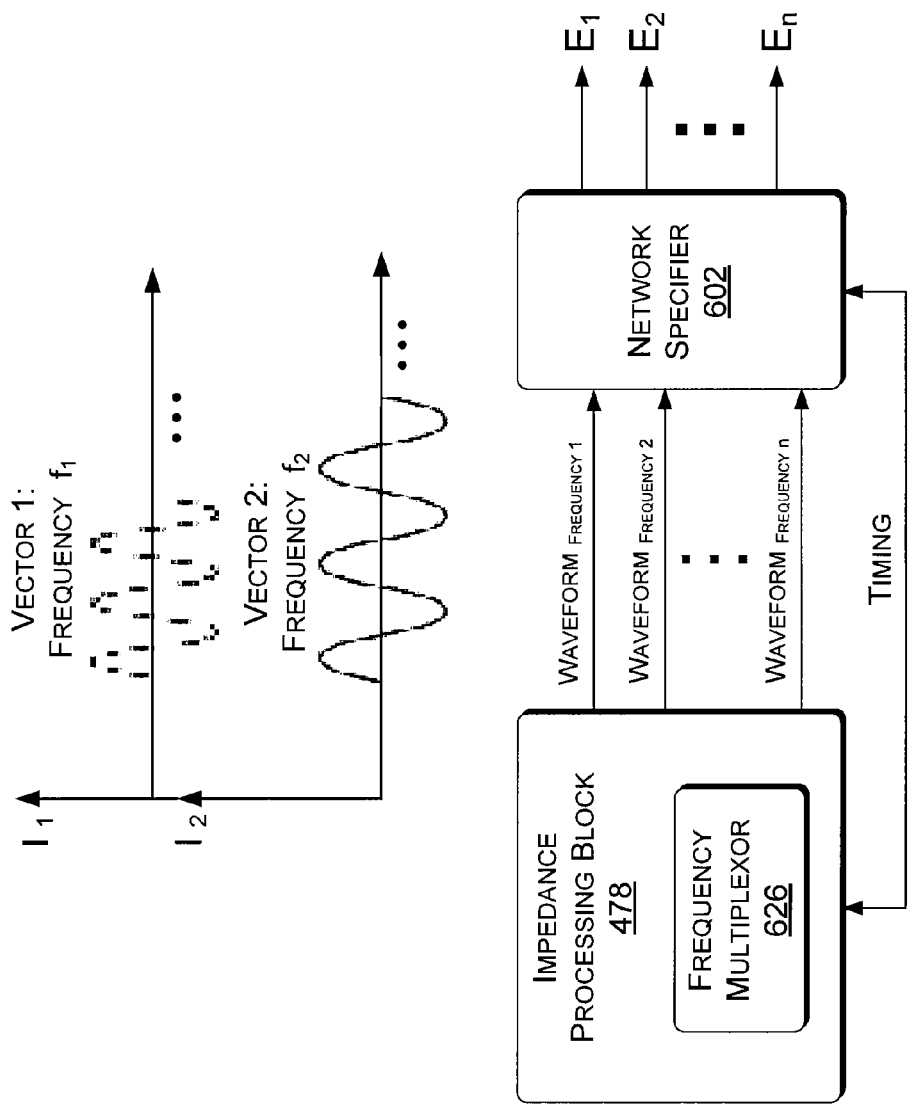
FIG. 11 is a block diagram of exemplary components for frequency-multiplexing signals over multiple vectors.

FIG. 11 shows a general schematic of exemplary components for applying frequency multiplexing, an alternative to time-multiplexing multiple waveforms 503 over the multiple vectors of a multi-vector network 350. In one implementation, the frequency multiplexor 626 of the waveform application engine 604 is a part of or communicatively coupled with an impedance processor block, such as impedance measuring and processing circuits 478. Depending on implementation, the frequency multiplexor 626 may be coupled with components of the network specifier 602 or directly with switch 426.

In one implementation, the frequency multiplexor 626 generates or channels multiple frequencies of the waveform 503, one frequency for each vector of a given multi-vector network 350. The multiple waveforms 503 of different frequency exist simultaneously in the patient's bodily tissue.

Figure 12:
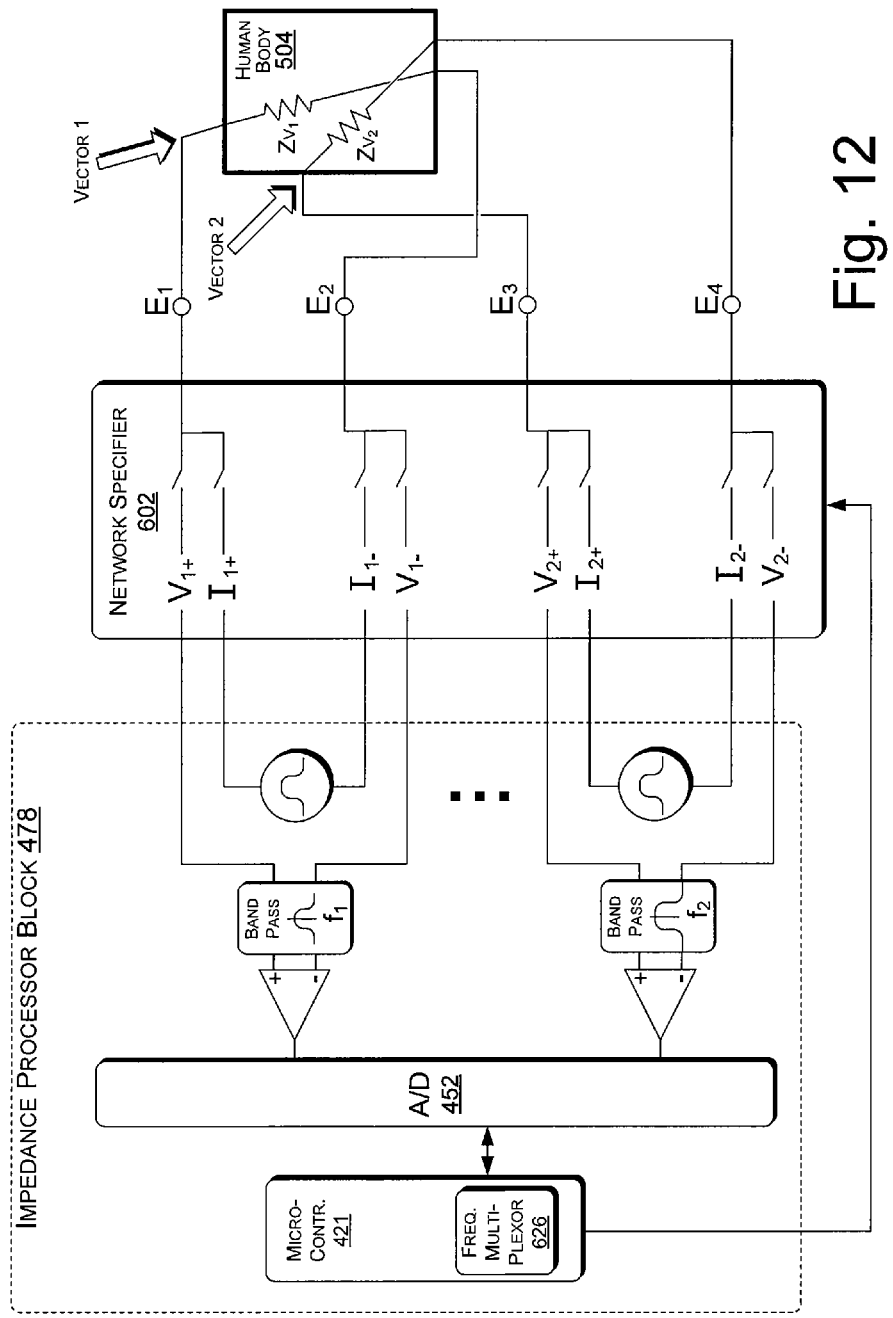
FIG. 12 is a block diagram of exemplary components for generating different frequencies of an exemplary waveform for frequency-multiplexing signals over multiple vectors.

FIG. 12 shows exemplary frequency-multiplexing components in greater detail. In one implementation, the frequency multiplexor 626 is implemented in the microcontroller 421 and initiates generation of multiple frequencies of the waveform 503, one frequency for each vector. The network specifier 602 applies each of the multiple frequencies to the electrodes associated with each vector and then senses an electrical result at each of the different frequencies to determine an impedance of each vector from the electrical result sensed at the frequency associated with that vector. Because the waveforms are at different frequencies, the waveforms can exist in the bodily tissue simultaneously without interfering with each other's electrical measurement. In this manner, a hemodynamic parameter can be measured simultaneously over multiple vectors of a multi-vector network 350.

Figure 13:
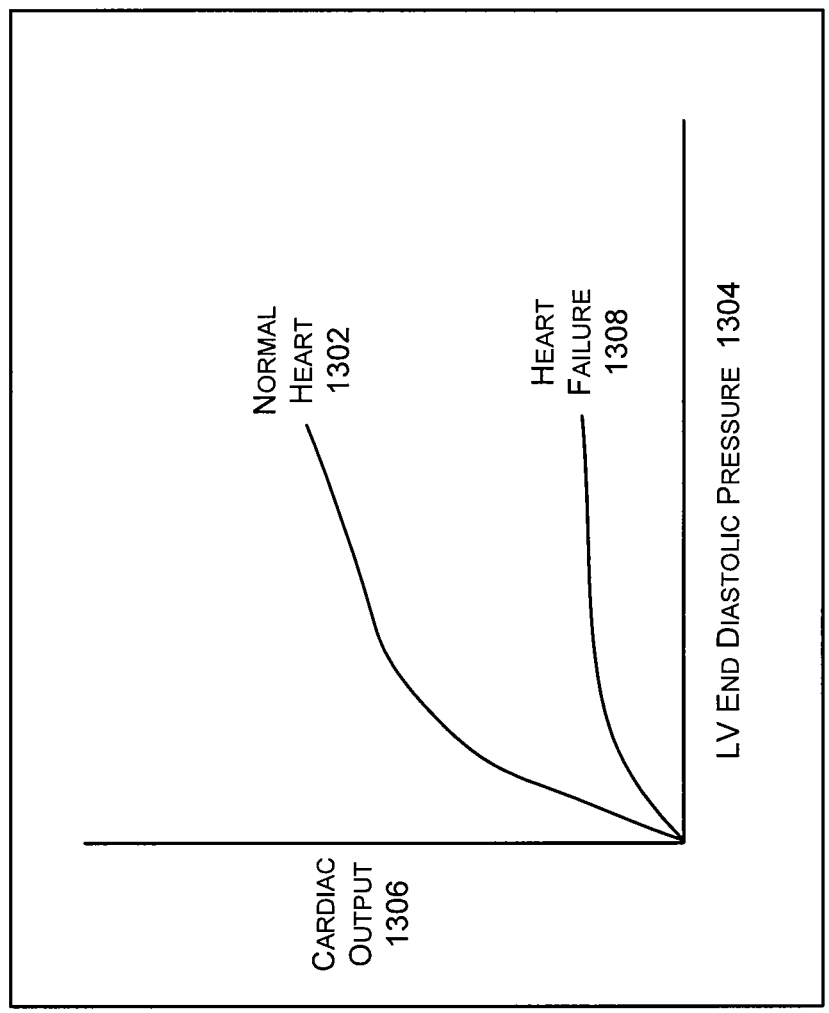
FIG. 13 is a diagram of cardiac output versus left ventricular end diastolic pressure.

Using Intracardiac Impedances to Trend Hemodynamic Parameters Related to Heart Failure As shown in FIG. 13, normally healthy hearts 1302 display a monotonically increasing relation between left ventricular end diastolic (LVED) pressure 1304 and cardiac output 1306. However, in heart failure patients, this relation is compromised. As shown in FIG. 13, the cardiac output curve for a patient in heart failure 1306 varies little over a wide range of values for LVED pressure 1304.

Accordingly, the impedance evaluator 606 determines an impedance value that correlates with an intracardiac pressure, such as the LVED pressure 1304 or the left atrial pressure (LAP), over at least one relevant vector, typically including an intracardiac vector. With the reliable sensing providing by an implantable device 300 that includes components of the exemplary multi-vector network engine 438, it is possible to make a strong correlation between the impedances sensed over at least one selected vector(s) of a given multi-vector network 350 and target hemodynamic parameters.

The physiological parameter evaluator 608 determines a value or a rough "status" of the LAP or LVED pressure from the impedance value provided by the impedance evaluator 606. The hemodynamic trender 638 may trend multiple values of the LVED or LAP pressure over time. The diagnosis and therapy module 640 tracks the value or the trend and aims to control the selected intracardiac pressure (rather than cardiac output 1306) by appropriately adjusting bi-ventricular pacing therapy (e.g., via timing control 432), such as the pacing therapy that is typically available in cardiac resynchronization therapy (CRT) devices.

CRT devices typically pace both ventricles of the heart based on predetermined timing sequences. Typically, the right atrium is paced first. Then, after a set A-V delay, the CRT device paces the left ventricle. To allow for the delayed LV contraction caused by heart failure, the right ventricle is paced last, after a set V-V delay. The diagnosis and therapy module 640 signals the timing control 432 to adjust either or both the A-V and V-V delays such that the LAP or the LVED pressure 1304 are brought into normal ranges.

The premise supporting this approach is based on a knowledge that lower intracardiac pressures promote heart remodeling that, in time, reduce (reverse) the enlargement of ventricles and atria. As heart dimensions trend back to normal values, the strength of the cardiac muscle increases, resulting in increased cardiac output 1306. Rather than using pressure as the direct control feedback parameter for regulating therapy, the exemplary device 300, including the multi-vector network engine 438, uses impedance to regulate therapy with the goal of reducing intracardiac blood pressure levels.

Gathering Impedance Results in the Heart with an Intracardiac Vector

The multi-vector network engine 438 selects one or more vectors to measure a hemodynamic parameter, and when the hemodynamic parameter is an intracardiac parameter, then at least one of the vector(s) is selected that has a high sensitivity to the parameter being measured, of course. For example, a preferred left ventricle (LV) to right atrium (RA) intracardiac vector has increased sensitivity to hemodynamic parameters indicative of pulmonary edema. Sometimes, if it is not certain which single vector has the increased sensitivity to a given parameter, there is benefit to the network specifier 602 positing and selecting multiple vectors to measure the parameter. A majority consensus may arise among the vectors and the trended values they provide over time may provide further assurance of consensus among the multiple vectors.

On the other hand, if a sensitive single vector is known beforehand, it can still be beneficial to measure a parameter with multiple vectors in order to determine an extent of the parameter's change. If vectors that are least sensitive to changes in the parameter register a change, then the extent of parameter change is likely greater than if only the most sensitive vector is affected. However, for many of the parameters discussed herein, a single vector may suffice for sensing an impedance effect that correlates with the parameter, sufficient for purposes of monitoring heart failure and controlling therapy. On the other hand, when the exemplary waveform 503 is used over a selected multi-vector network 350, impedance data often more accurately predicts hemodynamic changes caused, for example, by heart failure. The combination of the exemplary waveform 503 and the helpful redundance of multiple vectors of a multi-vector network 350 often greatly improves reliability over just using a single impedance vector as with many conventional measurement means.

Additionally, the inclusion of one or more intracardiac vectors in a multi-vector network 350 improves specificity and sensitivity in detecting cardiac conditions, thereby allowing an earlier detection of the onset of heart failure than conventional techniques, which typically sense general thoracic impedance. For example, to more precisely detect an early worsening of left ventricular ejection fraction (LVEF) trends, the multi-vector network engine 438 can measure cardiac impedance over a multi-vector network 350 that includes intracardiac vectors.

Figure 14:
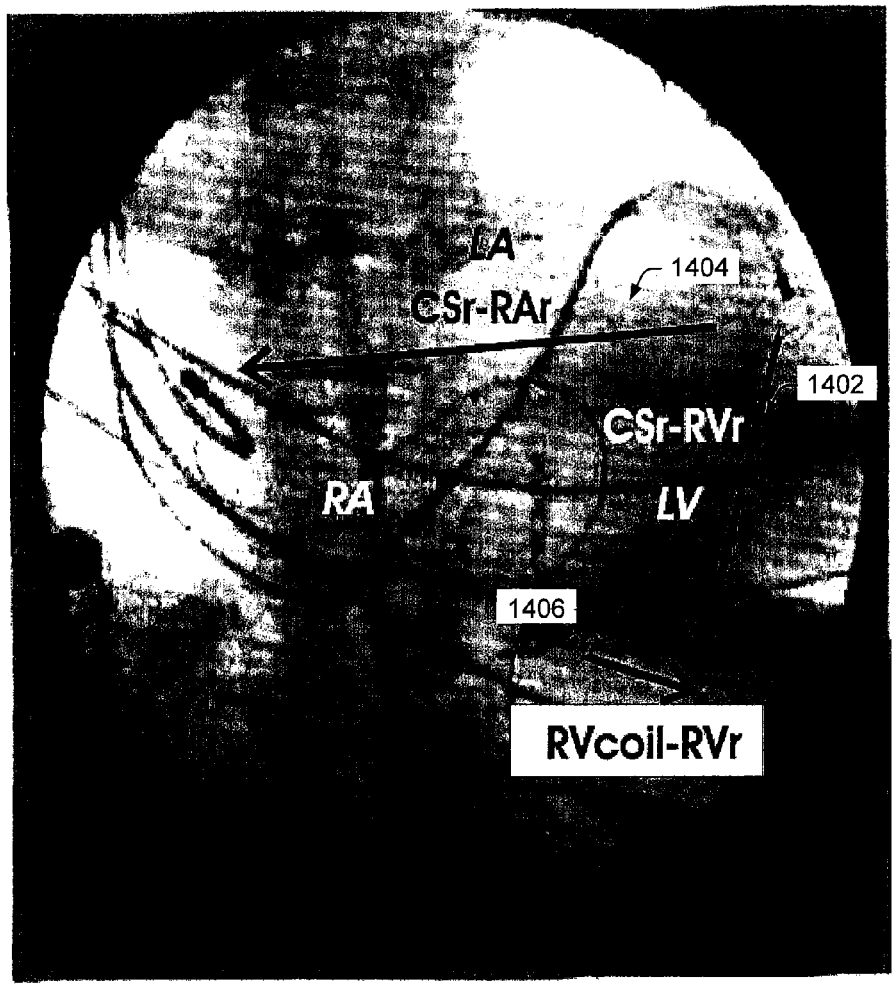
FIG. 14 is a diagram of an exemplary multi-vector configuration.

For many heart failure conditions, the efficacy of the exemplary multi-vector network engine 438 becomes apparent in its ability to apply the exemplary waveform 503 over one or more of these intracardiac vectors. For example, as shown in FIG. 14, as the left ventricle (LV) becomes weaker and enlarges due to heart failure, a decreasing impedance over a vector 1402 between the coronary-sinus-ring (CSr) electrode 318 and the right-ventricular-ring (RVr) electrode 330 is expected. However, if this were the only vector acquired, the data would not be specific enough because enlargement of the left atrium (LA) or the right ventricle (RV) could also contribute to a decreasing impedance in the above vector 1402. If, however, a vector 1404 between the coronary-sinus-ring (CSr) electrode 318 and the right-atrial-ring (RAr) electrode 324 and/or a vector 1406 between the right-ventricular-coil (RVc) electrode 332 and the right-ventricular-ring (RVr) electrode 330 point to a stable local trend, then the vector cross-correlator 632, in evaluating all three vectors, can more specifically interpret the impedance trend over the vector 1402 between the coronary-sinus-ring (CSr) electrode 318 and the right-ventricular-ring (RVr) electrode 330 as indicating changes primarily in the left ventricle (LV). In other words, the multi-vector network engine 438 can localize or pinpoint problems and structures originating hemodynamic parameters.

Other vector combinations can be used on the multi-vector network 350 to improve specificity in determining left atrial (LA) or right ventricular (RV) enlargements or changes. More reliable therapy or real-time control can be initiated based on these results. In one implementation, the diagnosis and therapy module 640 initiates or adjusts a cardiac therapy in real-time, based on results from the physiological parameter evaluator 608.

The exemplary multi-vector network 350, especially as enhanced by using one of the exemplary waveforms 503, can utilize a network of impedance measurements over multiple vectors to detect changes in numerous hemodynamic parameters (not just those associated with enlargement of a heart chamber, described above). A sample list of other parameters that can be trended by the exemplary multi-vector network engine 438 include:

SS—systolic slope, dZ/dt(max)—contraction
DS—diastolic slope, dZ/dt(min)—relaxation
PEP—pre-ejection period (low resolution)
ET—ejection time
LVEF—left ventricular ejection fraction (~PEP/ET)
DHFI—"diastolic heart failure index"
CI—cardiac index,
etc.

Figure 15:
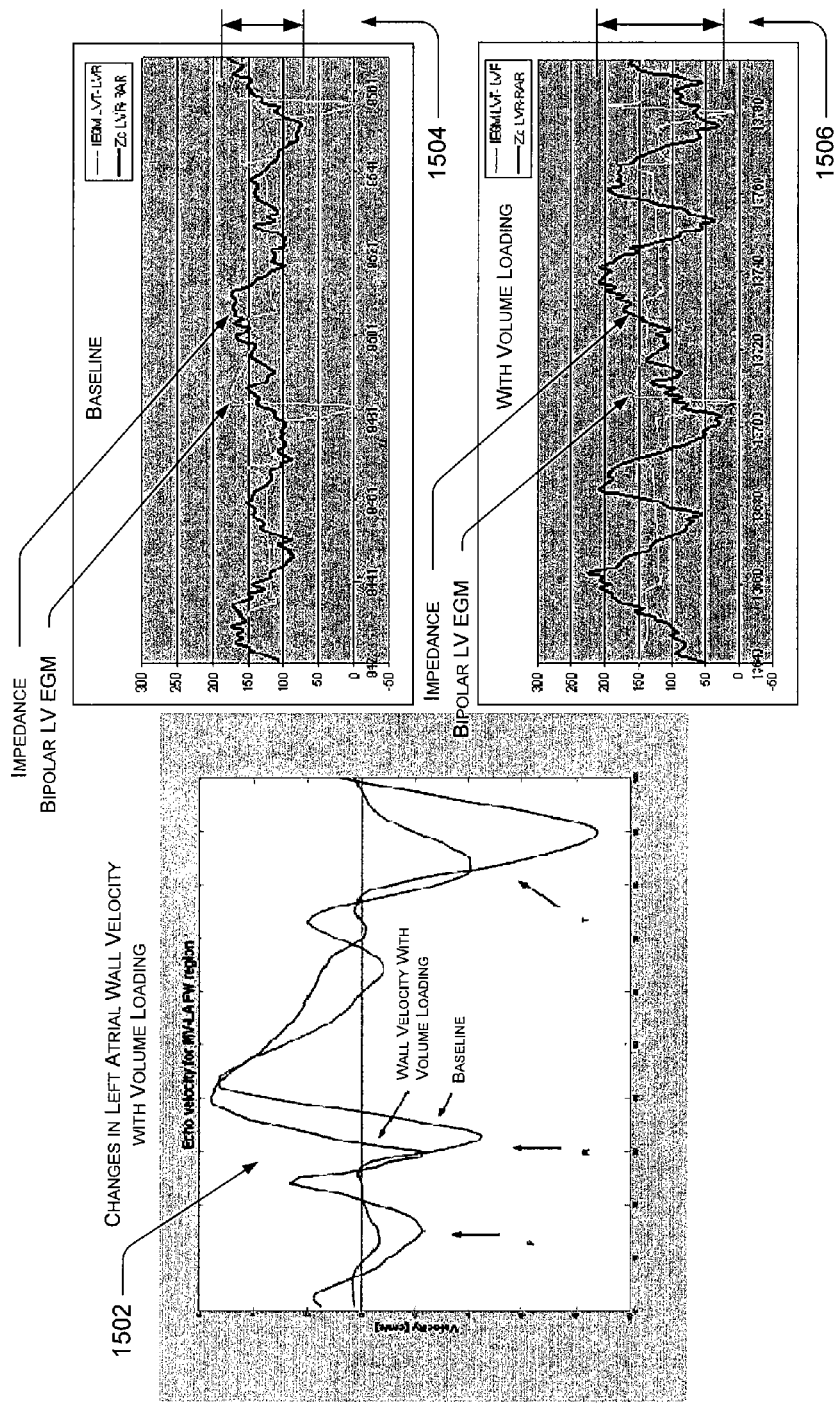
FIG. 15 is a diagram of impedance as related to changes in left atrial wall velocity during fluid loading.

Using Cardiogenic Impedance to Trend Intracardiac Pressure to Monitor and Treat Heart Failure FIG. 15 continues describing the principle introduced above with respect to FIG. 13, that is, sensing impedance effects to track and control an intracardiac pressure instead of tracking cardiac output or instead of tracking a cardiac pressure via echocardiography. Cardiogenic impedance can be a good predictor of changes in the trends of left-atrial (LA) mechanical parameters, such as the left atrial (LA) wall velocity 1502 (as verified by also determining wall velocity 1502 by echocardiography). Changes in cardiogenic impedance and changes in heart chamber volumes correlate. Thus, the increase in left-atrial wall velocity 1502 documented in the velocity graph of FIG. 15 is reflected in a relative increase in the magnitude of the notches seen in the cardiogenic impedance waveform during the P and the T waves of the cardiac cycle (that is, a first peak-to-peak variation 1504 increases in magnitude to a second peak-to-peak variation 1506).

Figure 16:
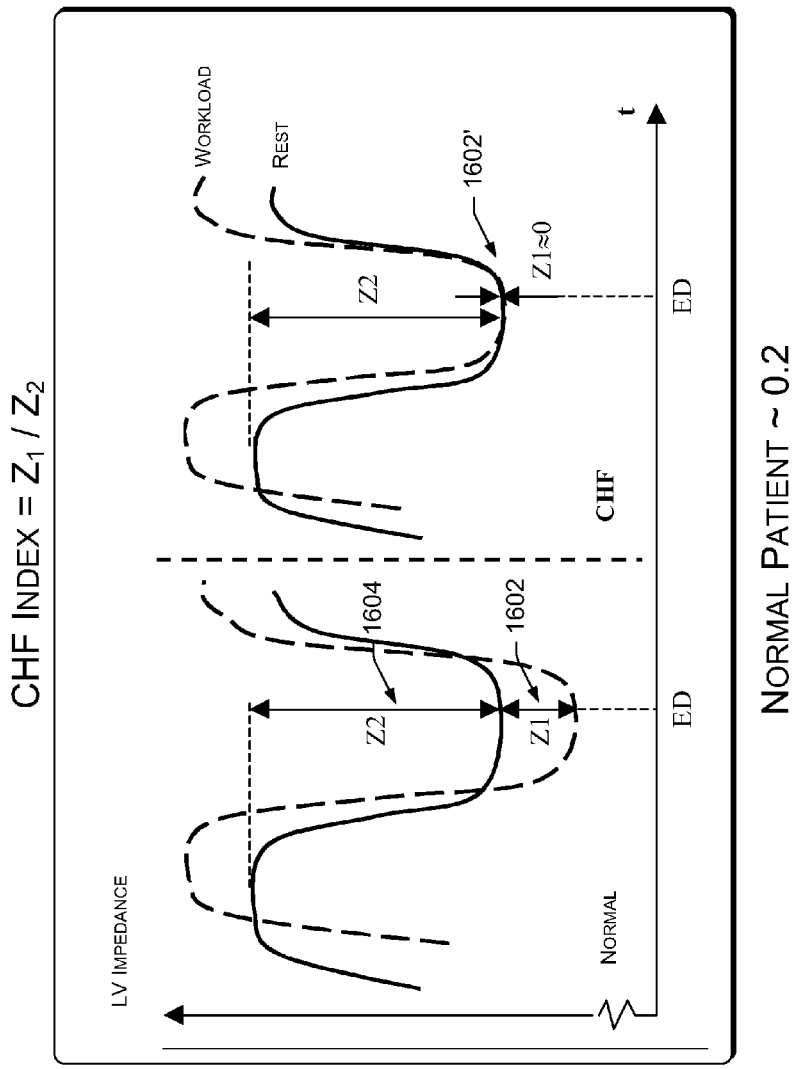
FIG. 16 is a diagram of using impedances to calculate a cardiac heart failure index.

Likewise, as shown in FIG. 16, a multi-vector network 350 can reliably sense intracardiac impedances to measure hemodynamic parameters that translate relatively directly into practical diagnostic tools. In patients with a degree of heart failure but preserved left ventricular (LV) systolic function, an exemplary multi-vector network engine 438 can calculate a congestive heart failure index that can gauge, for example, exercise intolerance in such patients, which will now be described.

In normal patients who do not have a heart failure condition, the impedance over a left ventricular (LV) intracardiac vector changes between a rest state and an exercise state by different amounts, due to differences in the left ventricular (LV) end-diastolic volume during each state. Thus, (as shown in FIG. 16) the ratiometric CHF index can be represented by a ratio of an impedance $Z_1$ 1602 representing the impedance difference between the two states at the LV end-diastolic volume, divided by the magnitude of an impedance $Z_2$ 1604 that represents the rest state LV end-diastolic volume (as compared with baseline volume). The normal value of this CHF index ratio is around 0.2. For patients with diastolic heart failure, however, the CHF index ratio is zero, because of exercise intolerance: in such patients, $Z_1$ 1602' is zero because the LV end-diastolic volume does not adapt during an increased exercise load. The network specifier 602 of the multi-vector network engine 438 can designate a combination of vectors that can associate these results specifically with the left ventricle (LV) to reliably determine a patient's CHF index.

Using Impedance Effects Sensed Over a Multi-Vector Network to Trend Pulmonary Edema Related to Heart Failure An exemplary multi-vector network 350 uses information from several impedance vectors to improve the accuracy of detecting tissue swelling and fluid build-up, such as fluid build-up in the lungs secondary to onset of heart failure. The fluid build-up characteristic of pulmonary edema (PE) is a relatively late symptom of heart failure compared with earlier intracardiac symptoms, such as changes in left atrial pressure (LAP), volume, and chamber enlargement, by which the multi-vector network engine 438 can often make an earlier prediction of heart failure than conventional techniques. Nonetheless, trending pulmonary edema is described herein for its practical value and its illustrative value in pointing up features of the multi-vector network engine 438.

Fluid build-up in the lungs decreases impedance measured across a vector between a right ventricular (RV) coil electrode 332, for instance, and a case electrode 600. However, the variation in impedance over this vector can be of a small absolute magnitude, given that the baseline value is in the 50-80 ohm range (i.e., a relatively small baseline value). Noise or limitations of conventional instrumentation affect the accuracy of such measurements. In turn, the reliability of trends computed from this single vector alone may have a low specificity and sensitivity to fluid build-up in the lungs: that is, conventionally established trends may be incorrect.

In addition to the above-described vector, the multi-vector network engine 438 can simultaneously measure impedances across additional vectors, such as a vector between the coronary sinus (CS) ring electrode 318 and the case electrode 600, and/or a vector between the coronary sinus (CS) ring electrode 318 and the right atrial (RA) ring electrode 324. Other combinations of vectors can also be used. The vector cross-correlator 632 can correlate trends from these multiple vectors, thereby providing improved overall prediction rates of pulmonary edema.

Figure 17:
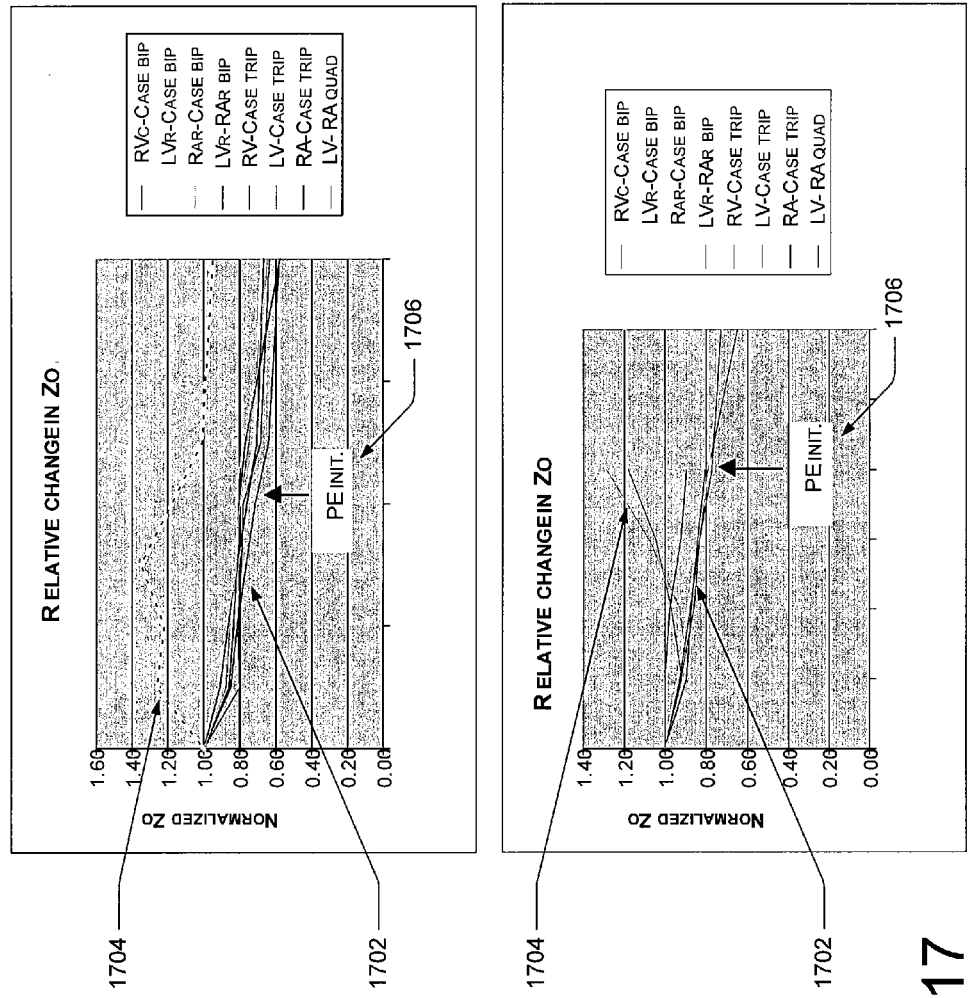
FIG. 17 is diagram of exemplary detection of the beginning of pulmonary edema based on trended impedance values obtained over a multi-vector network.

With regard to correlating the trending values obtained from multiple vectors, as shown in FIG. 17 the impedances measured by the multi-vector network engine 438 over a majority set 1702 of vectors may trend together (a consensus, or at least an agreement between two or more vectors) adding reliability to a pulmonary edema prediction, especially as compared with impedance of a few, non-trending vectors 1704.

In one implementation, when the trending impedance (e.g., of the majority set of vectors 1702) decreases by more than 20%, the diagnosis and therapy module 640 decides that pulmonary edema has commenced 1706.

Using Impedance Waveform Morphology to Monitor and Treat Heart Failure

Figure 18:
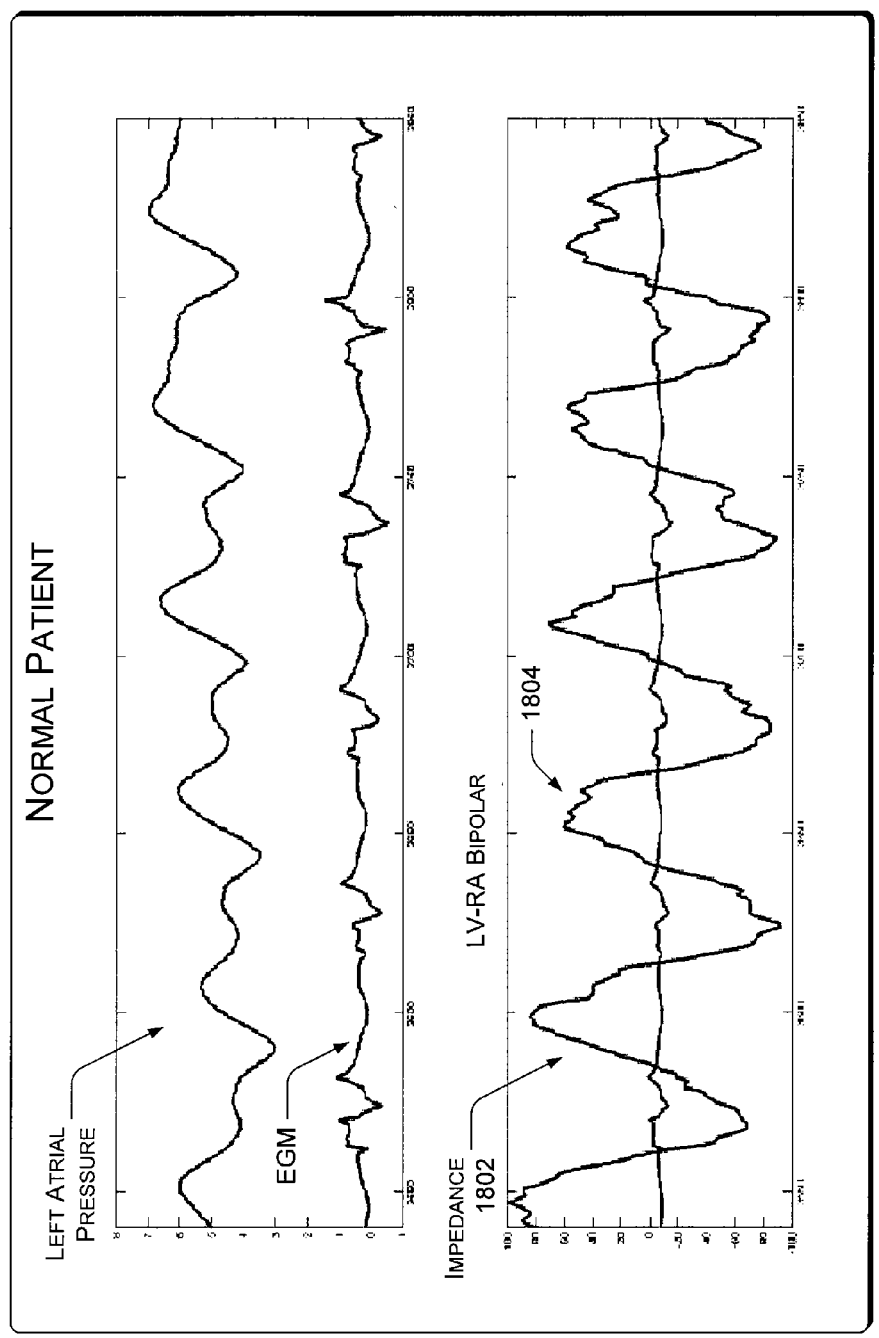
FIG. 18 is a diagram of exemplary impedance waveform detection as related to left atrial pressure in a normal patient.
Figure 19:
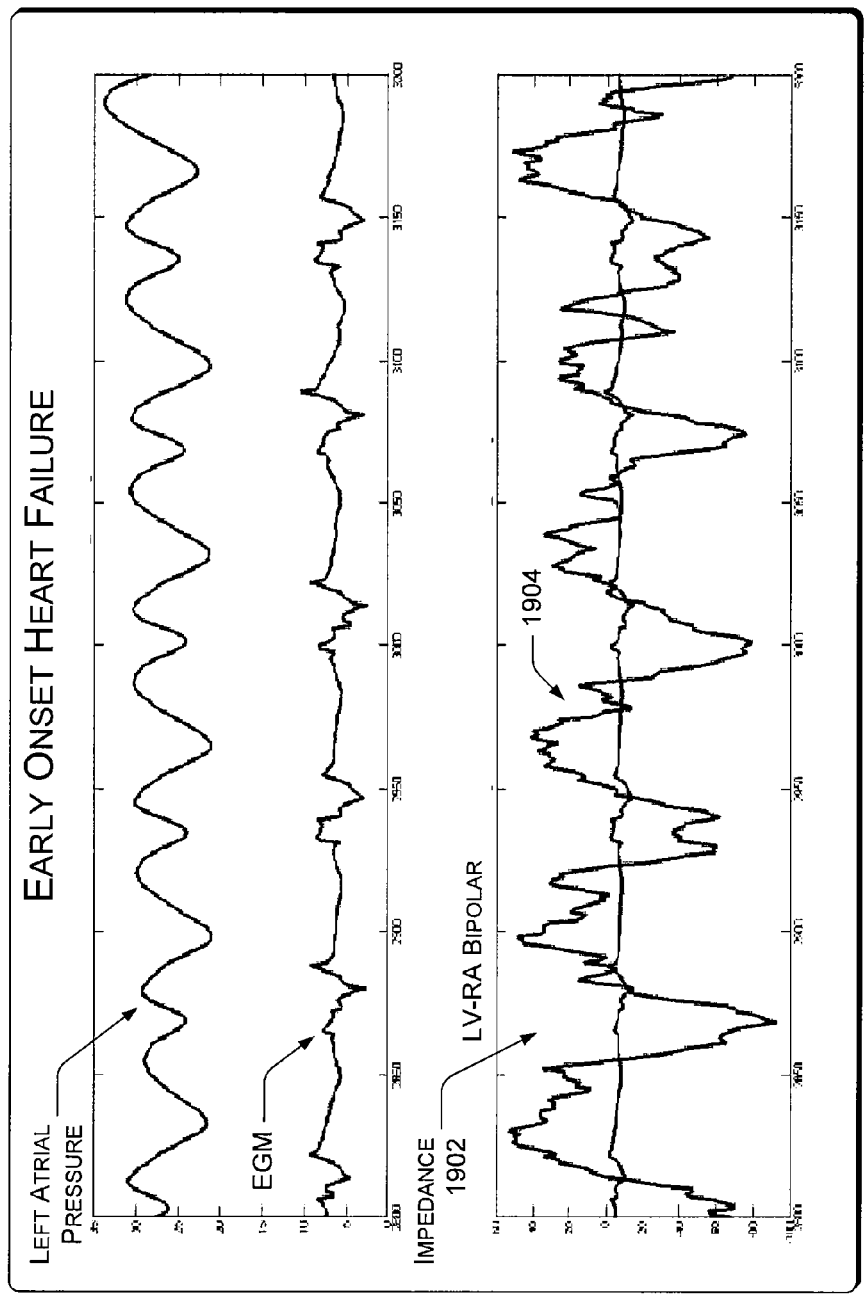
FIG. 19 is a diagram of an exemplary fractionation characteristic of impedance waveform detection as related to left atrial pressure during early onset of heart failure.
Figure 20:
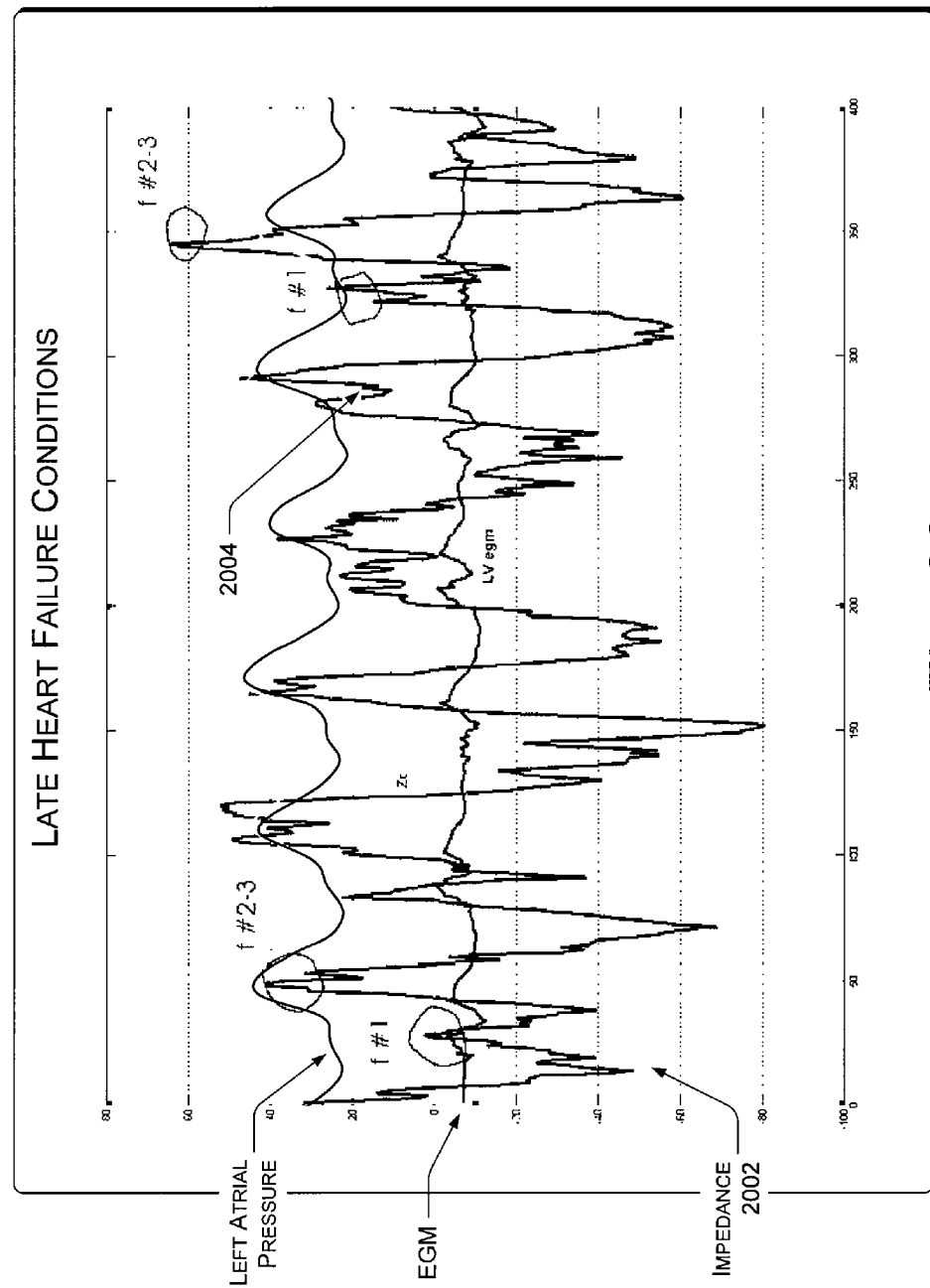
FIG. 20 is a diagram of exemplary fractionation characteristic of impedance waveform detection as related to left atrial pressure under late heart failure conditions.

Using a Fractionation Characteristic of the Impedance Waveform to Trend Intracardiac Pressure for Monitoring and Treating Heart Failure FIGS. 18, 19, and 20 show intracardiac impedance and its relationship to left atrial pressure (LAP) during a patient's cardiac cycle. LAP is known to be a reliable predictor of heart failure progression. Increasing LAP levels are known to be indicative of worsening heart failure conditions. The intracardiac impedance is sensed over a vector, e.g., between the left ventricle (LV) and the right atrium (RA). (Other vectors can be used.) FIG. 18 shows intracardiac impedance under normal conditions. FIG. 19 shows the intracardiac impedance at the early onset of heart failure. FIG. 20 shows the intracardiac impedance during late heart failure conditions.

In FIG. 18, for a normal patient free of heart failure, the characteristic morphology of the intracardiac impedance trace 1802 shows relatively smooth waves that follow the cardiac cycle, with relatively little raggedness (i.e., "fractionation") at the crest 1804 of each impedance trace peak (or trough). In FIG. 19, during early onset of heart failure, the intracardiac impedance trace 1902 develops a characteristic morphology of notches 1904 in or near the crests—i.e., a moderate degree of fractionation—that may be diagnostic of this stage of heart failure. In FIG. 20, during late heart failure conditions, the intracardiac impedance trace 2002 develops a characteristic morphology of high volatility and fractionation, where the magnitude of the notches 2004 increases significantly and their frequency of occurrence is high.

For example, in FIG. 20, features labeled f#1 are seen mostly around the P wave of the cardiac cycle. Features #2 and #3 are separated by a notch that occurs near the T wave of the cardiac cycle. Feature #2 precedes the notch, whereas feature #3 follows it. These features are not seen in a normal LV-RA cardiogenic impedance waveform, such as that shown in FIG. 18. The frequency of occurrence of these features (e.g., notches indicative of a fractionated waveform) increases as the average LAP increases from normal (FIG. 18), to elevated (FIG. 19), to very high late heart failure levels (FIG. 20). Thus, the morphology of the intracardiac impedance waveform obtained by the multi-vector network engine 438 can accurately stage heart failure, and notably can predict or determine the early onset of heart failure.

With therapy, as the LV-RA cardiogenic impedance resolves back from the fractionated morphology in FIG. 20 to the normal morphology in FIG. 18, the resolution indicates that the LA and/or LVED pressures decrease towards normal values. The multi-vector network engine 438 residing in the exemplary implantable device 300 adjusts the A-V or V-V timing delay such that the morphology of the LV-RA vector impedance trends back from that shown in FIG. 20 to that in FIG. 18. This can be achieved using one of many different techniques. For example, the peaks or troughs seen in the impedance morphology of FIG. 20 can be counted by the physiological parameter evaluator 608 or simply by another counter inside microcontroller 421 in FIG. 4. When the frequency of occurrence of these peaks and troughs is high, the A-V or V-V timing is adjusted from a set value (determined, for example, at implant time) to lower or higher values, with the goal of decreasing the frequency of the feature's occurrence.

In one implementation, the diagnosis and therapy module 640 first makes a timing adjustment in one direction, for example from original AV or V-V timing delays to higher values. If this adjustment results in a decreased frequency of occurrence for the peaks and troughs shown in FIGS. 19 and 20, then the adjustment is continued in this direction until the LV-RA impedance waveform trends close to normal morphologies, as shown in FIG. 18. Otherwise, the direction of the timing delay adjustment is reversed and values are decremented from initial settings to lower numbers. Alternatively, other impedance characteristics (as will be described below), or other vectors from the multi-vector network that correlate with LA and LVED pressures, such as peak-to-peak amplitudes, can be used to adjust the A-V and V-V timing.

Figure 21:
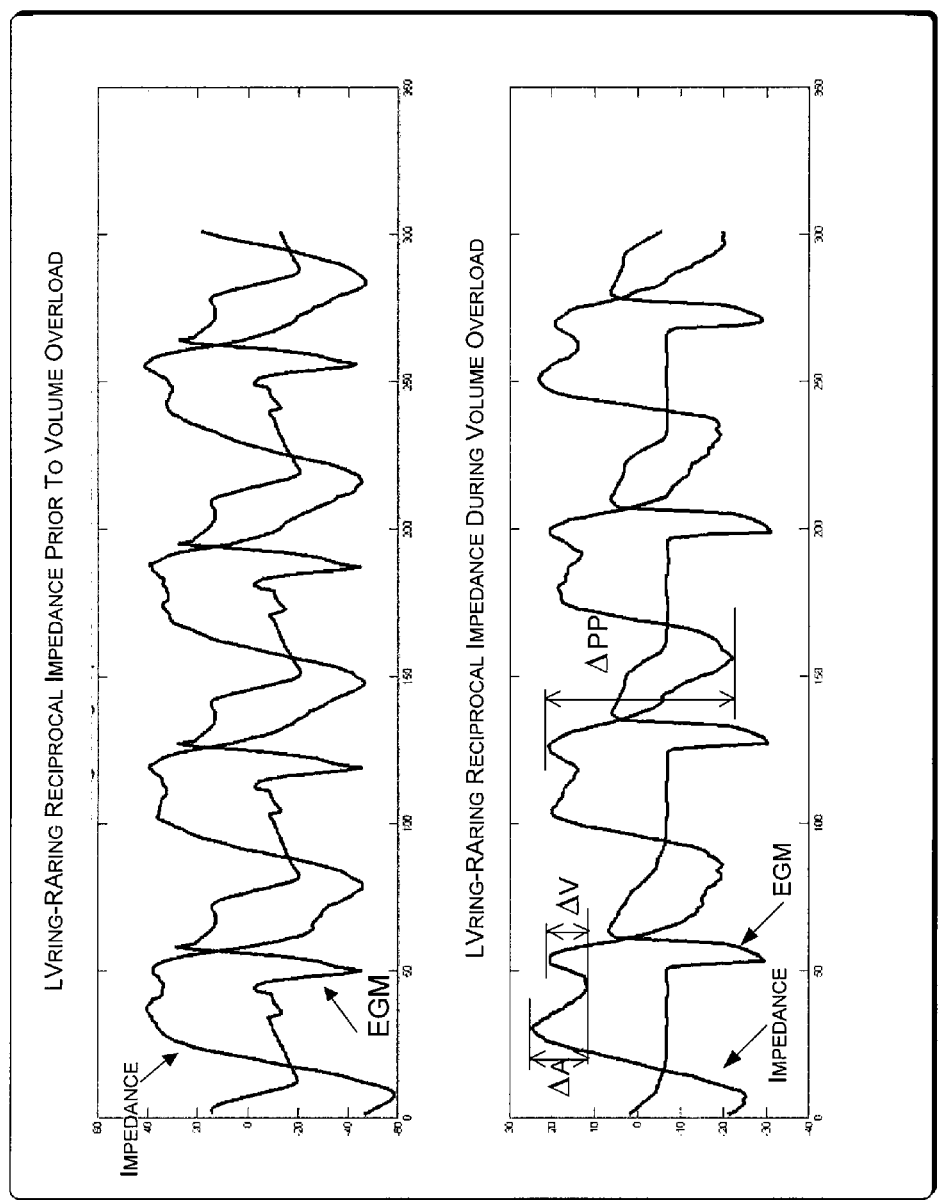
FIG. 21 is a diagram of exemplary ratiometric characteristics of impedance over a left ventricular (LV) to right atrial (RA) vector during fluid overload.

Using Ratiometric Data and Peak-to-Peak Amplitude Characteristics of the Sensed Impedance Waveform to Trend Intracardiac Pressure for Monitoring and Treating Heart Failure FIG. 21 illustrates some impedance tracing properties during early heart failure that give rise to impedance ratiometric data that can be trended to detect or predict cardiac conditions or pulmonary edema, etc. During volume overload of pulmonary edema secondary to early heart failure, the intracardiac impedance, for example the impedance over the vector between the left ventricular (LV) ring electrode 316 and the right atrial (RA) ring electrode 324, develops a notched characteristic that has diagnostic morphological features that can be measured by the exemplary multi-vector network engine 438. For example, $\Delta A$ represents a peak corresponding to the atrial "kick" of contraction while $\Delta V$ represents a peak corresponding to the ventricular contraction kick. The term $\Delta PP$ represents the peak-to-peak impedance amplitude. In one implementation, to track early heart failure trends, the multi-vector network engine 438 can follow several ratio trends. First, an increasing trend in the ratio $\Delta A/\Delta V$ indicates an increasing LV/RV volume trend indicative of early heart failure. Second, a decreasing trend in the ratio $\Delta V/\Delta PP$ follows a decreasing trend in the left ventricular ejection fraction (LVEF). Also, $\Delta A/\Delta V$ tends to increase with increasing average left atrial pressure (LAP). As shown in FIG. 20, an impedance vector from the left ventricle (LV) to the right atrium (RA) becomes more notched 2004 or fractionated as left atrial pressure (LAP) increases.

Table (1) below shows ratiometric data that the hemodynamic trender 638 of the multi-vector network engine 438 may use to establish thresholds for diagnosing the early onset of pulmonary edema. The diagnosis and therapy module 640 can use these thresholds to modify a cardiac therapy in a real-time response to changing trends in the parameters monitoring the heart failure. Typical values for the ratios are shown for three intracardiac vectors in Table (1):

TABLE 1

| | Vector | | | | | |
|---|---|---|---|---|---|---|
| | LVr-RAr | | LVr-RVr | | RVc-RVr | |
| | $\Delta a/\Delta v$ | $\Delta v/\Delta pp$ | $\Delta a/\Delta v$ | $\Delta v/\Delta pp$ | $\Delta a/\Delta v$ | $\Delta v/\Delta pp$ |
| Before fluid overload | 0.5 | n/a | 0.36 | 0.58 | 0.33 | 0.38 |
| After fluid overload | 1.1 | n/a | 0.43 | 0.52 | 0.85 | 0.23 |

After the multi-vector network engine 438 creates a multi-vector network 350 that includes one or more of the above tabled intracardiac vectors, the diagnosis and therapy module 640 can then use such a table to establish thresholds between a normal state and a fluid overload state. If a fluid overload state is occurring, the diagnosis and therapy module 640 can signal an alarm or apply a therapy or modification in a real-time response to early detection of the fluid overload or increasing pressure.

Figure 22:
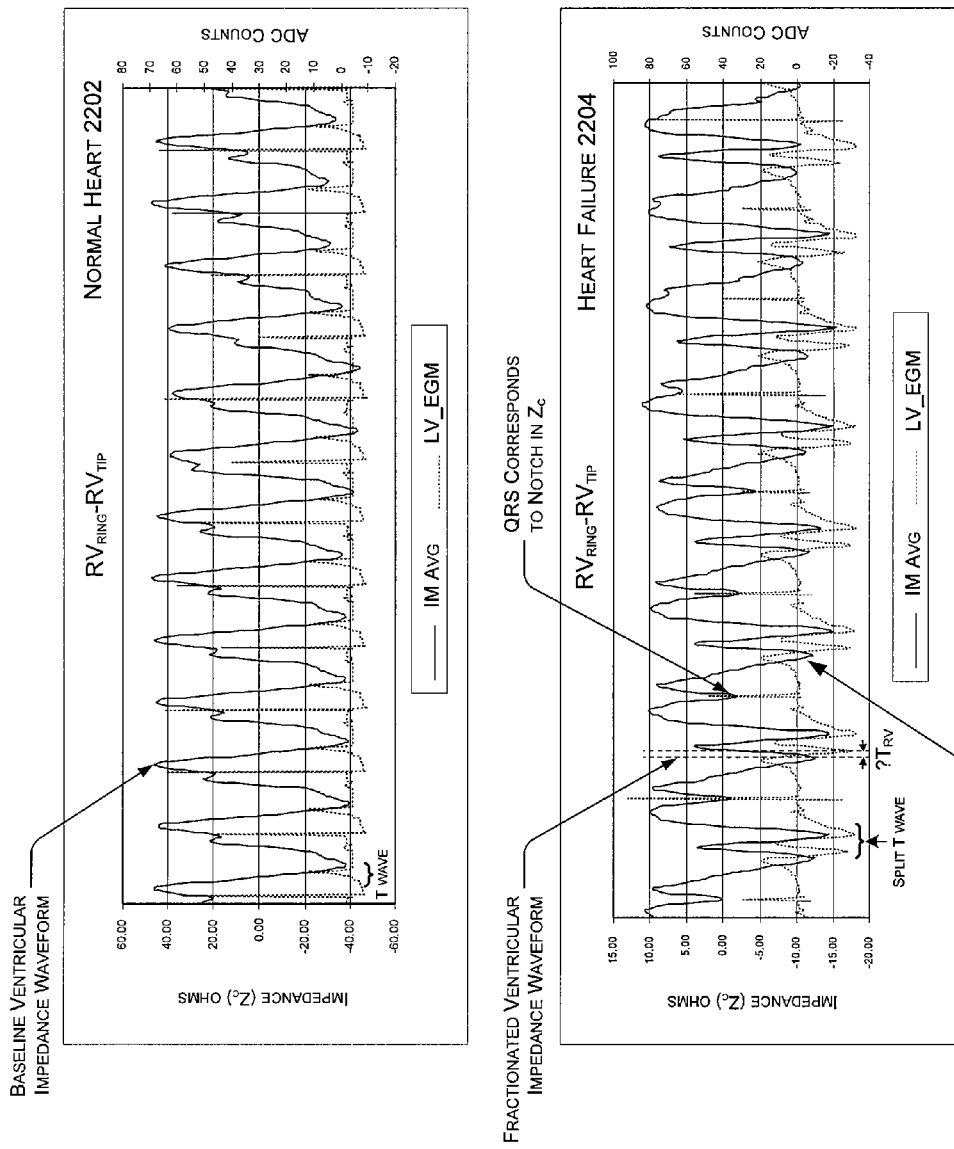
FIG. 22 is a diagram of a dyssynchrony characteristic of impedance waveform detection over a first vector.
Figure 23:
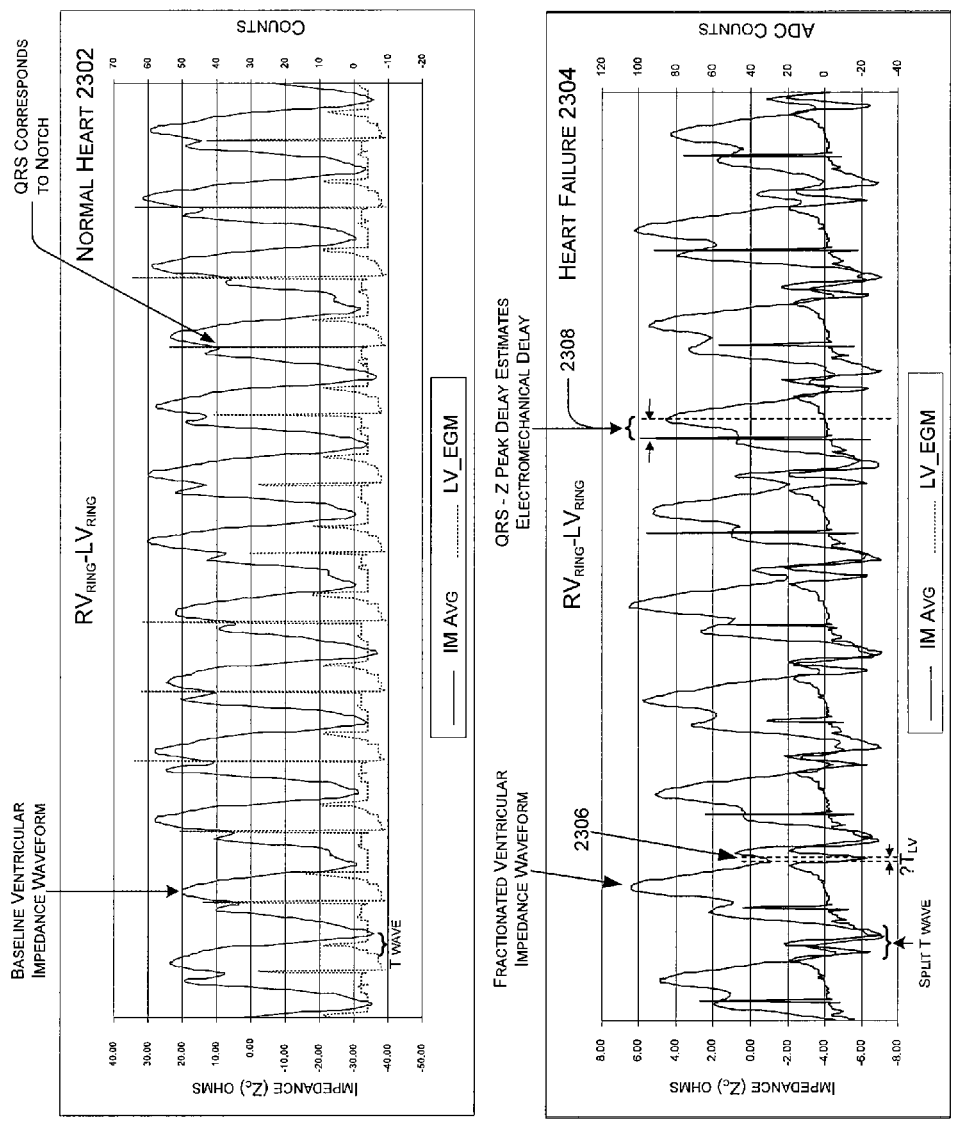
FIG. 23 is a diagram of a dyssynchrony characteristic of impedance waveform detection over a second vector.

Using Impedance to Trend Cardiac Dyssynchrony as a Surrogate for Intracardiac Pressure for Monitoring and Treating Heart Failure FIGS. 22 and 23 show intracardiac impedances obtained over two vectors: an RV-ring-to-RV-tip vector in FIG. 22 and a RV-ring-to-LV-ring vector in FIG. 23. In each figure, a top panel shows the intracardiac impedances obtained in a normal heart (2202 and 2302) and a bottom panel shows the intracardiac impedances obtained in a heart afflicted with heart failure (2204 and 2304). A bipolar electrogram (EGM) of the corresponding cardiac cycle is imposed on the waveform strip.

In the diseased hearts, 2204 and 2304, the first notch in both cardiogenic impedance waveforms corresponds to the QRS complex in the bipolar EGM. The second notch (2206 and 2306) occurs within the time interval of the T wave.

In the normal hearts (2202 and 2302), as an indication of synchronous ventricular contraction, both cardiogenic impedance waveforms display a single notch that corresponds to the QRS and a single 'peak' that occurs after the QRS.

In heart failure (2204 and 2304), both cardiogenic impedance waveforms display fractionation with distinct peaks during the T wave. These peaks are caused by ventricular dyssynchrony. Additionally, the corresponding T waves display one main notch, rather than being round-shaped as are the normal T waves.

A Dyssynchrony Index can be calculated as: $DYS.IND = \Delta T_{RV} - \Delta T_{LV}$, where the $\Delta T$ for each ventricle represents the time delay of the notch in the T wave with respect to the second notch of the cardiogenic impedance waveform. This delay is representative of the electromechanical delay of the respective ventricle. Additionally, the time delay 2308 between the occurrence of the QRS complex (available to the exemplary implantable device 300) and the occurrence of a corresponding peak in the impedance waveform can be indicative of worsening association between the electrical and mechanical activities of the corresponding ventricle. Since the delay in the impedance peak reflects the electromechanical delay, the dyssynchrony or more specifically the Dyssynchrony Index defined above can be trended for purposes of monitoring and treating heart failure.

In normal hearts (2202 and 2302) the DYS.IND is typically less than 30 msecs. In heart failure (2204 and 2304) the DYS.IND typically increases to 60-80 msecs, or higher. Thus, the DYS.IND value can be used to optimize V-V intervals for Bi-V pacing. In one implementation, the diagnosis and therapy module 640 applies a V-V delay (by stimulating the left ventricle first, then the right ventricle) that is approximately equal to the value of the DYS.IND determined above. Adjustment of the V-V delay being applied by the therapy module 640 is made in real time.

In one implementation, the split aspect of the T wave, seen in electrograms, is also predictive of ventricular dyssynchrony and heart failure. Thus, characteristics of the split-T-wave morphology can also be used to control CRT therapy in implantable devices 300.

Using Exemplary Impedance Measurements to Check Lead, Electrode, and Device Integrity Conventionally, electrode integrity assessment in an implantable device is performed either during delivery of pacing pulses or with low voltage discharges. If the integrity assessment mode depends on delivery of pacing pulses, then in the case of patients in which pacing is turned off or inhibited by the patient's intrinsic rhythm, but the low voltage electrodes are still being used for sensing, electrode integrity cannot be assessed unless pacing pulses are delivered. If the integrity assessment mode depends on low voltage discharges, then performing low voltage discharge measurements on certain sensitive patients in the absence of tachyarrhythmia episodes can produce an uncomfortable sensation. Further, due to the nature of the measurement, this technique restricts the assessment to "in-clinic" follow-up only Additionally, each of these conventional assessment modes provide only limited assessment of the electrode sensing performance.

In an exemplary integrity assessment technique, the lead integrity engine 642 of the multi-vector network engine 438 uses the applied waveform 503 in FIG. 5 and one or more of the vectors in an exemplary multi-vector network, e.g., as illustrated in FIG. 3. In the case of high voltage electrodes, this exemplary technique has the added advantage of being able to assess integrity more frequently (e.g., as often as once per hour or even more often) without having to deliver a voltage discharge that might be felt by the patient. The results of this integrity assessment can be displayed real-time on the external programmer 454, during implant or follow-up sessions, or can be stored in the implantable device 300 for trending over time, e.g., in order to notify the patient (using the patient notifier) or the physician (through the programmer or a house-call system). The exemplary assessment technique provides the added benefits of "out-of-clinic" surveillance of lead status and increased patient safety.

The lead integrity engine 642 applying an exemplary assessment technique can be used to confirm the integrity of individual electrodes by applying sub-threshold current pulses via the waveform 503 between that electrode and the device case 400. Alternatively, to minimize the number of applications of current, the physician may opt to check any combination of two electrodes by applying the sub-threshold current waveform pulses between the pair electrodes. Additionally, the exemplary assessment technique can also check the condition of the lead-device system, such as:

faulty insulation in the device header;
abrasion between lead jacket and device case;
faulty feedthrough;
lead pin misconnection in header ports;
faulty lead electrode or wire including sub-clavian crush; and
abrasion of wire insulation inside leads.

Conditions such as stable, open, or short-circuited electrodes can be observed either on a real-time external display or by retrieving the trend data from the implantable device 300. Examples of detectable conditions are provided below. Although representative of actual data and situations, the examples below are only for illustrating the concept. In some implementations, the exemplary assessment technique uses additional current drawn from the battery. However, this supply current need not have a material impact on the battery life. To minimize the impact on the battery even further, the exemplary assessment techniques can be conducted with combinations of two electrodes at a time, rather than using single electrodes.

Figure 24:
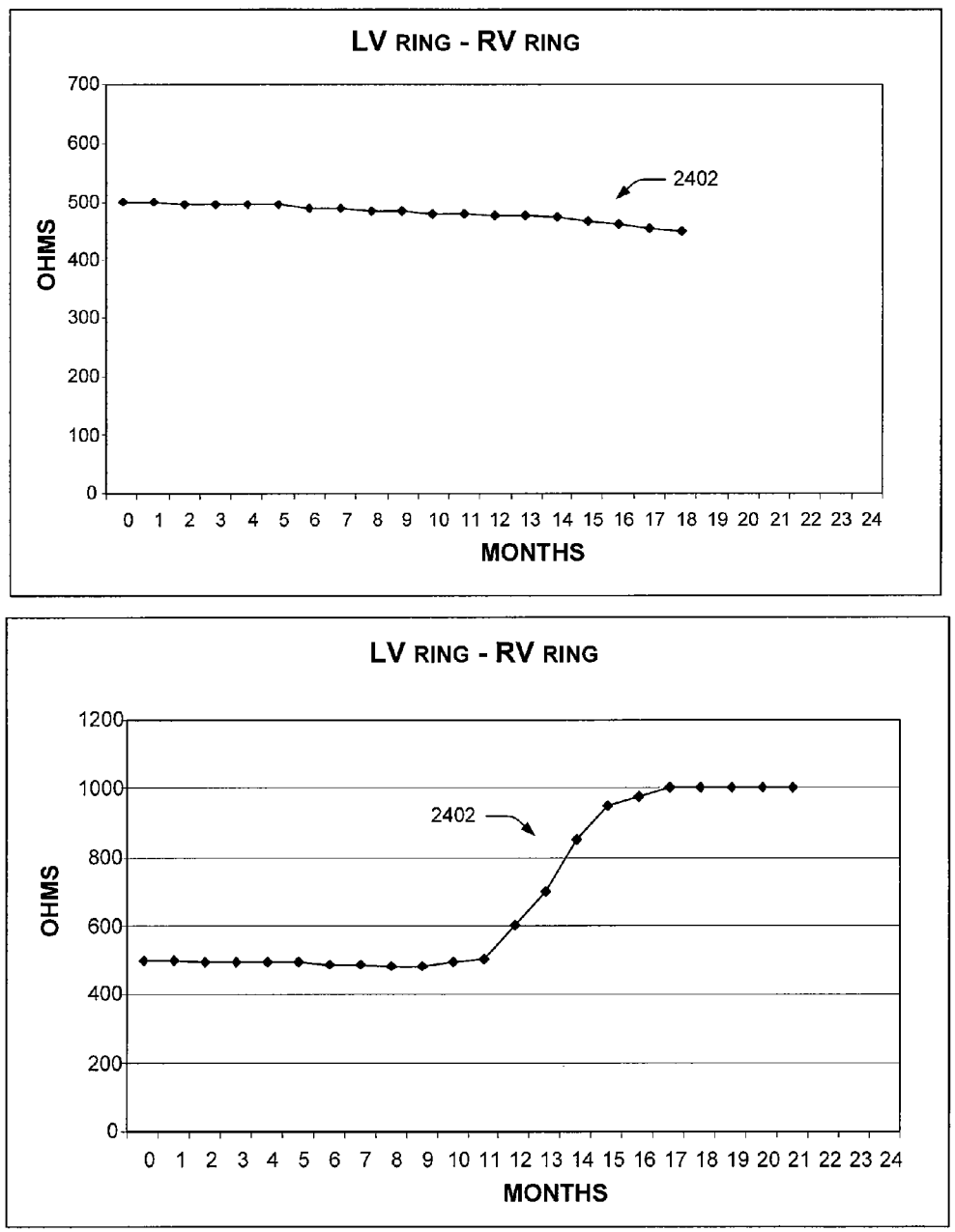
FIG. 24 is a diagram of detection of normal versus compromised electrode integrity using an exemplary waveform over an LV ring to RV ring vector.

FIG. 24, top panel, illustrates an example of sensed impedance in which the electrode pair LV ring and RV ring display a stable trend 2402 over time. This implies that both electrodes will perform well when used in regular pacing or bi-ventricular pacing.

FIG. 24, bottom panel, illustrates an example of sensed impedance using the same electrode pair as above: LV ring and RV ring. In this example, one of the electrodes in the pair displays degrading electrical contact 2404 over time. The degrading trend 2404 can be caused by compromised: electrode-wire welding, lead position, header connection, etc. In such case, the practitioner may opt to perform a more detailed integrity check of header connectivity and lead placement at follow-up, possibly entailing lead repositioning or replacement, should one of the electrodes display an open circuit.

Figure 25:
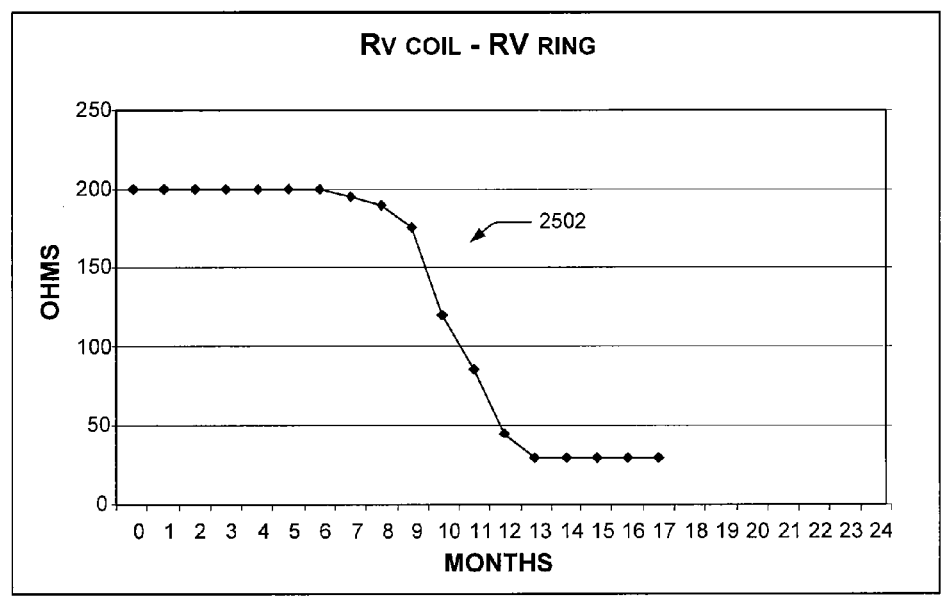
FIG. 25 is a diagram of detection of sheath abrasion using an exemplary waveform over an RV coil to RV ring vector.

FIG. 25 shows an example of sensed impedance showing an abrasion trend 2502, i.e., abrasion of the insulation between the wires for the RV coil and the RV ring electrodes. The impedance between these two electrodes presents a gradual decrease in the abrasion trend 2502. Another possible cause for such the abrasion trend 2502 might be abrasion of the lead jacket that causes increased current leakage to the device case 400.

FIG. 26 shows that the lead integrity engine 642 may apply an exemplary assessment technique in-clinic at implant or follow-up time, to check whether the connectivity of leads at the header is correct. For example, in FIG. 26, the practitioner can recognize that the LV lead and RA lead IS-1 connector pins are inadvertently swapped by the impedance value. E.g., if the real-time value of the impedance between the LV ring and the RV ring electrodes reads approximately 150 ohms, a value that is low, the placement is incorrect. Due to the intra-ventricular septum, the normal value for the impedance between these two electrodes should be in the range of approximately 500 ohms. Thus, when the LV ring is incorrectly connected to the RA port, the blood present on the right side shunts the impedance measured between these two electrodes. So, the exemplary assessment technique displays a low real-time value. The practitioner can use this low reading correct the connectivity of leads in the header ports.

Figure 27:
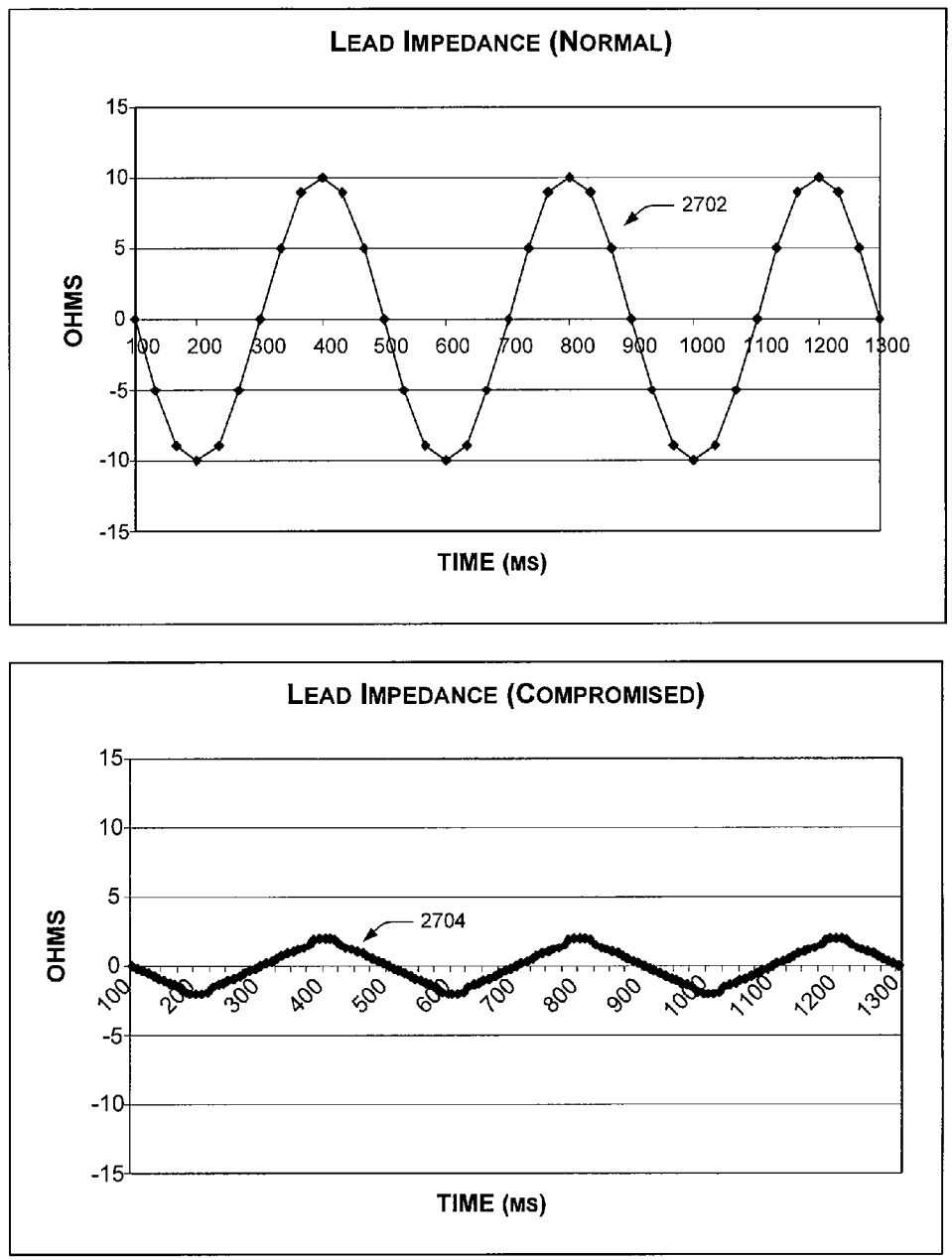
FIG. 27 is a diagram of detection of normal versus compromised lead integrity using an exemplary waveform.

FIG. 27, top panel, shows a real-time impedance graph of a lead in which the sensing performance of either the RV ring or the RV tip electrodes is acceptable. The variation seen in the impedance waveform 2702 is caused by the heart pumping. The waveform is representative of the variation in cardiogenic impedance between the RV ring and RV tip electrodes.

FIG. 27, bottom panel, shows by comparison noisy behavior 2704 of the same electrode pair as in the real-time graph of the top panel. This indicates that the sensing performance of at least one of these two electrodes is compromised. Example causes for this behavior are abrasion of the wire insulation inside the lead, poor lead pin connection at the header port, or suboptimal lead position. In one implementation, the lead integrity engine 642 applies this assessment feature only in-clinic, at implant time, or during follow-up. In such circumstances, either at implant or during follow-up time, the practitioner may opt to further check or reposition the RV lead, check the connectivity at the header port, or replace the lead with a new one.

Multi-Vector Impedance Networks for Cardiography: 3-D Impedancegrams

A multi-vector network 350 can provide a relatively selectable volumetric approach to determining physiological parameters, similar in concept with vectorcardiograms, at least as compared with conventional single vector "linear" approaches. That is, given an array of physical or even virtual (e.g., added together) electrodes coupled in a network, multiple electrodes can apply a signal into tissue and the same or different multiple electrodes can then sense the injected signal, providing in some applications, a rough or a refined "gram" that contains 3-dimensional (3-D) information or a rotational impedance vector, sometimes amounting to a 3-D view that is associated with the 3-D mechanical activity of the heart. The 3-D view may be crude or may be quite refined, amounting to a rough visualization of location or a visible image depending on implementation. When the applied signal is the exemplary waveform 503, for example, the multi-vector network engine 438 can triangulate or cross-correlate vectors to determine variations in the mechanical activity of the heart through a volume of tissue with a shape that has been selected by the multi-vector network engine 438.

In one implementation that employs numerous vectors, the multi-vector network engine 438 creates a 3-D impedancegram. Increased detail in an impedancegram or a visualization of tissue is usually easier to achieve when more electrodes are available in a particular implantation for creating more vectors. For example, a patch electrode bearing numerous individual electrodes can be implanted near the heart or even subcutaneously to provide a large variable arrays of electrodes, which can be used to increase detail and selectivity in a vector-impedancegram and the resulting visualization.

In one implementation, a multi-vector network 350 uses multiple vectors between sets of electrodes, each set consisting of, e.g., two physical electrodes. This provides vectors that constitute relatively linear electrical paths between vector endpoints. Such relatively linear vectors can be deployed in parallel or intersecting paths depending on application, to localize hemodymamic parameter values to specific areas of tissue or structure where the two vectors "intersect."

It should be noted that an actual electrical path between two point electrodes depends a great deal on the tissue between the electrodes. Because an applied signal follows the path of least resistance or least impedance, sometimes most of the applied signal does not follow a perfectly straight line between the two electrodes. Typically, there is a volume of tissue between the two electrodes that becomes the electrical path, instead of a straight line. Transfer of current is typically not homogenous throughout such a volume. If voltage is applied and electrical current measured, then the potential across different parts of such a volume is typically nonuniform.

In another implementation, the multi-vector geometry engine selects a multi-vector combination that provides a set of vector planes between the vector endpoints. This allows for a configuration of vectors in which parallel planes of the multi-vector network 350 "slice" a tissue of bodily structure, or where intersecting planes monitor a line of tissue that is common to the planes.

In yet another implementation, electrode combinations create a multi-vector network 350 that consists of one or more vectors describing volumetric paths between vector endpoints. Each endpoint of such vectors may consist of a planar array of physical electrodes, such that a single vector has an electrical path that is more broadly volumetric than a typical volume of tissue that conducts current between two point electrodes. Such a volumetric vector may encompass a tissue or bodily region, an organ, or an entire bodily structure. If sufficient electrodes are available, multiple volumetric vectors can be combined in parallel or intersecting configurations, e.g., with an intersecting single linear vector.

In some implementations, electrical paths of various different geometries can be realized among the various vectors of a multi-vector network 350. Such an implementation may include a combination of linear, planar, and volumetric vectors. This is not to say that a typical implementation with a conventional 3-lead implantation would have enough combined vectors for detailed imaging—to create a visualization of structure that could be recognized as a "picture" by a human observer (although such is not ruled out in some implementations that have sufficient electrodes). But a combination of different impedance vectors for making a measurement does mean that the same tissue is being sensed or "looked at" from different angles, and a group of such data processed by the vector cross-correlator 632 is likely to be able to locate a tissue, a structure, or an originating point of a hemodynamic value.

Exemplary Methods

Figure 28:
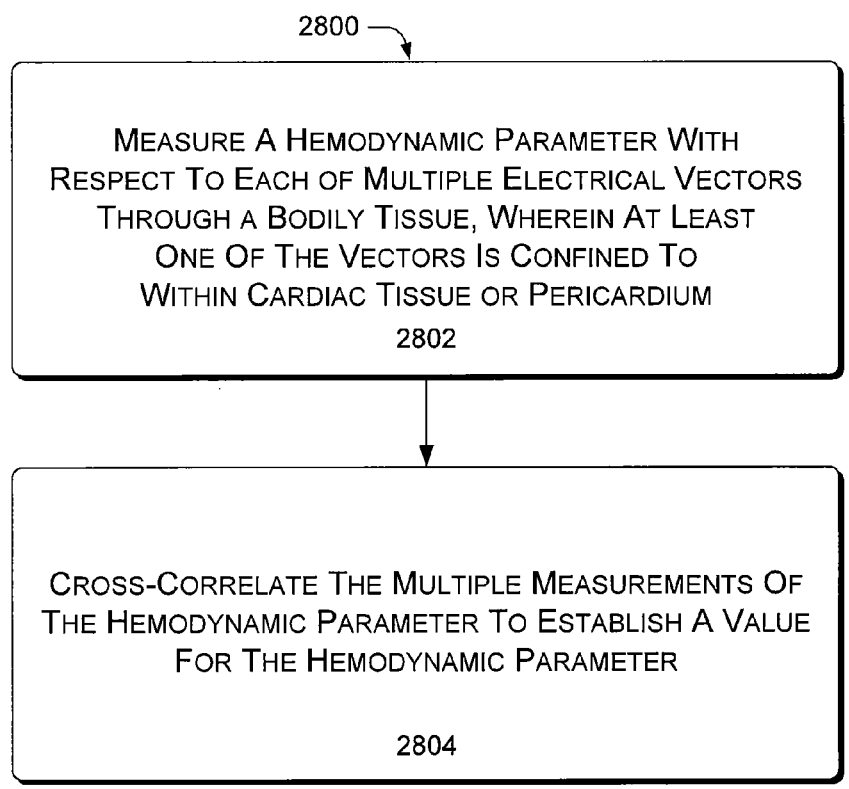
FIG. 28 is a flow diagram of an exemplary method of measuring a hemodynamic parameter over a multi-vector network.

FIG. 28 shows an exemplary method 2800 of measuring a hemodynamic parameter over a multi-vector network. The exemplary method 2800 may be implemented in connection with many suitably configured implantable devices, although it will be described as being executed by the exemplary multi-vector network engine 438 and/or the exemplary impedance measurement circuit architecture 500. In the flow diagram of FIG. 28, the operations are summarized in individual blocks. Some operations may be performed in hardware and/or as machine-readable instructions (software or firmware) that can be executed by a processor, such as microcontroller 421.

At block 2802, a hemodynamic parameter of a patient is measured with respect to each of multiple electrical vectors through a bodily tissue of the patient. At least one of the vectors is typically confined to within the patient's heart tissue or pericardium. An implantable device 300 performs the measuring and evaluates the multiple measurements of the hemodynamic parameter to establish a value for the hemodynamic parameter.

The method 2800 may further include evaluating an onset of heart failure based on the value of the hemodynamic parameter obtained. To accomplish this, measuring at each of the multiple vectors can include, in one implementation, measuring an impedance of the bodily tissue over each of the vectors.

Measuring impedances in this manner can be accomplished by a special waveform 503 applied over each of the vectors. The waveform 503 has a duration that is less than a charging time constant of electrode-electrolyte interfaces in the implantable system.

To achieve simultaneity or near-simultaneity of measurement, signals to be applied one per vector, can be injected into bodily tissue out of phase with each other, e.g., in a rapid succession. Thus, signals applied over the multiple vectors may exist simultaneously in bodily tissue. Measurement of these co-existing signals may be carried out by time-multiplexing. Alternatively, impedance measurements across multiple vectors can be taken sequentially.

Multiplexing co-existing waveforms can also be carried out via frequency multiplexing, in which the signal or waveform for each vector is assigned a different frequency. Filters on the measuring side separate the component frequencies.

At block 2804, the multiple measurements of the hemodynamic parameter are evaluated to obtain a single value or a set of interrelated values for the hemodynamic parameter being measured. The evaluation of the multiple measurements can include cross-correlating the vector impedances; applying statistical models, e.g., to find a majority set of vectors that are trending together; subjecting the measurements to probabilistic models, etc. Typically, the method 2800 aims to produce trendable data points indicative of a heart failure condition. Thus, the measurements made over multiple vectors are first calculated as impedance, which on a higher level are correlated with a hemodynamic parameter, and the trended values for these hemodynamic values are interpreted as indicative of a heart failure condition. When a trend changes enough, the practitioner is alerted or the implantable device 300 makes a real-time adjustment to ongoing therapy.

Figure 29:
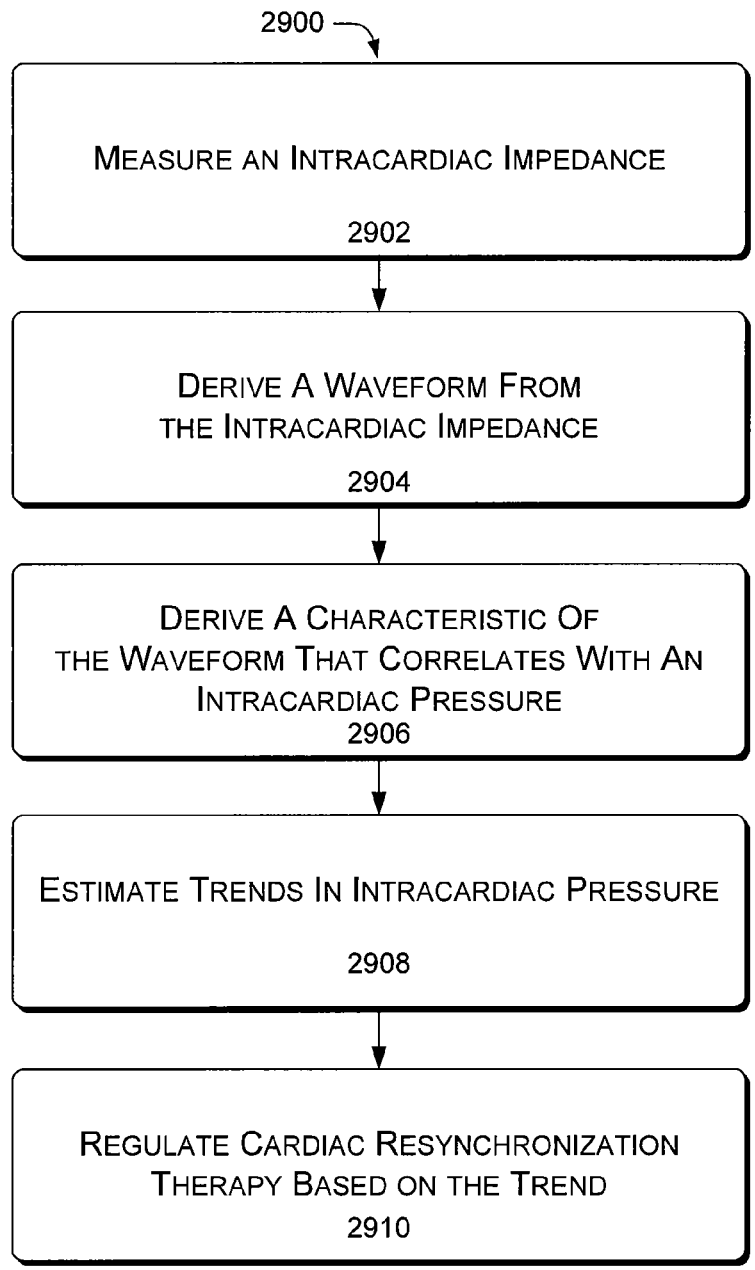
FIG. 29 is a flow diagram of an exemplary method of trending an intracardiac pressure based on an impedance waveform characteristic in order to regulate cardiac therapy.

FIG. 29 shows an exemplary method 2900 of trending an intracardiac pressure based on an impedance waveform characteristic in order to regulate cardiac therapy. The exemplary method 2900 may be implemented in connection with many suitably configured implantable devices, although it will be described as being executed by the exemplary multi-vector network engine 438 and/or the exemplary impedance measurement circuit architecture 500. In the flow diagram of FIG. 29, the operations are summarized in individual blocks. Some operations may be performed in hardware and/or as machine-readable instructions (software or firmware) that can be executed by a processor, such as microcontroller 421.

At block 2902, an intracardiac impedance is measured. The exemplary waveform 503 is leveraged to provide increased sensitivity and specificity in measuring the impedance. An intracardiac vector is selected for measuring the intracardiac impedance, when needed for a particular implementation.

At block 2904, a waveform shape—morphology—is derived from the intracardiac impedance.

At block 2906, a characteristic of the waveform shape is derived, that correlates with an intracardiac pressure or other hemodynamic parameter that can be used to monitor heart failure or regulate its treatment. The characteristic may be an amount of fractionation in the waveform, various ratiometric data associated with the waveform, peak-to-peak amplitudes associated with the waveform, dyssynchrony of the waveform with the patient's native QRS complex or between vectors, etc.

At block 2908, intracardiac pressure values are trended from the derived characteristics of the waveform.

At block 2910, cardiac resynchronization therapy (CRT) is regulated according to the trend.

Figure 30:
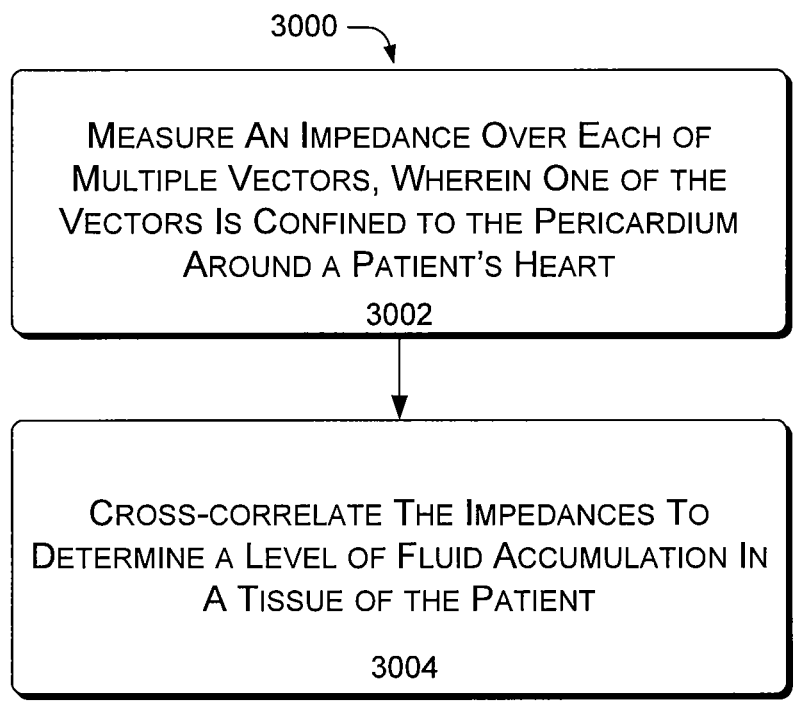
FIG. 30 is a flow diagram of an exemplary method of using impedance measurements made over a multi-vector network in order to determine a level of fluid accumulation.

FIG. 30 shows an exemplary method 3000 of using impedance measurements made over a multi-vector network in order to determine a level of fluid accumulation. The exemplary method 3000 may be implemented in connection with many suitably configured implantable devices, although it will be described as being executed by the exemplary multi-vector network engine 438 and/or the exemplary impedance measurement circuit architecture 500. In the flow diagram of FIG. 30, the operations are summarized in individual blocks. Some operations may be performed in hardware and/or as machine-readable instructions (software or firmware) that can be executed by a processor, such as microcontroller 421.

At block 3002, an impedance is measure over each of multiple vectors, including if needed, one vector confined to the heart's own tissue or at least confined within the pericardial sac.

At block 3004, the impedances thus measured at block 3002 are cross-correlated to determine a level of tissue swelling, such as fluid accumulation in a tissue of the patient. In one implementation, the exemplary waveform 503 is leveraged across the multiple vectors in order to obtain impedance values that are more accurate and more specific to tissue swelling and/or fluid accumulation in tissue. Although cross-correlation is provided here as an example of multi-vector data processing, other methods, such as probabilistic decision, thresholding, etc., can be employed as efficiently by the skilled in the art.

Figure 31:
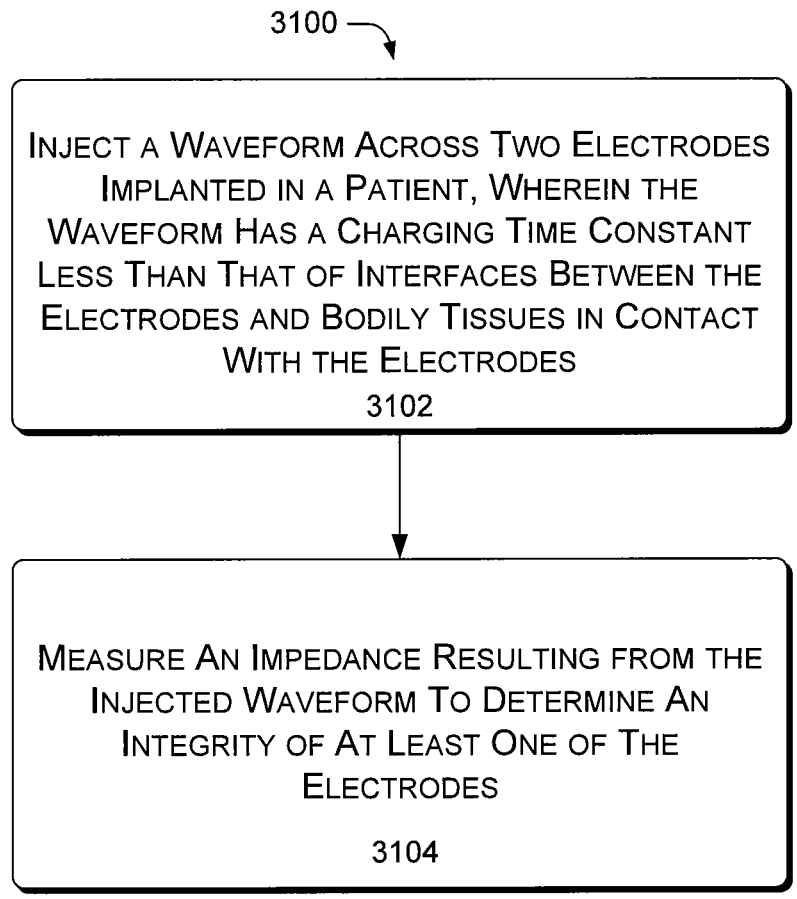
FIG. 31 is a flow diagram of an exemplary method of applying an exemplary waveform to check lead integrity.

FIG. 31 shows an exemplary method 3100 of applying an exemplary waveform to check lead integrity. The exemplary method 3100 may be implemented in connection with many suitably configured implantable devices, although it will be described as being executed by the exemplary multi-vector network engine 438 and/or the exemplary impedance measurement circuit architecture 500. In the flow diagram of FIG. 31, the operations are summarized in individual blocks. Some operations may be performed in hardware and/or as machine-readable instructions (software or firmware) that can be executed by a processor, such as microcontroller 421.

At block 3102, an exemplary waveform 503 is applied across two electrodes implanted in a patient. The exemplary waveform 503 is charge- and voltage balanced and has a duration less than a charging time constant of the interfaces between the two electrodes and the bodily tissue in contact with the two electrodes.

At block 3104, an impedance that results from the injection of the applied waveform 503 is used to determine the integrity of one or both of the electrodes. The exemplary waveform 503 generally cannot be felt by the patient, rendering the lead integrity check sub-threshold, thereby increasing patient safety.

Figure 32:
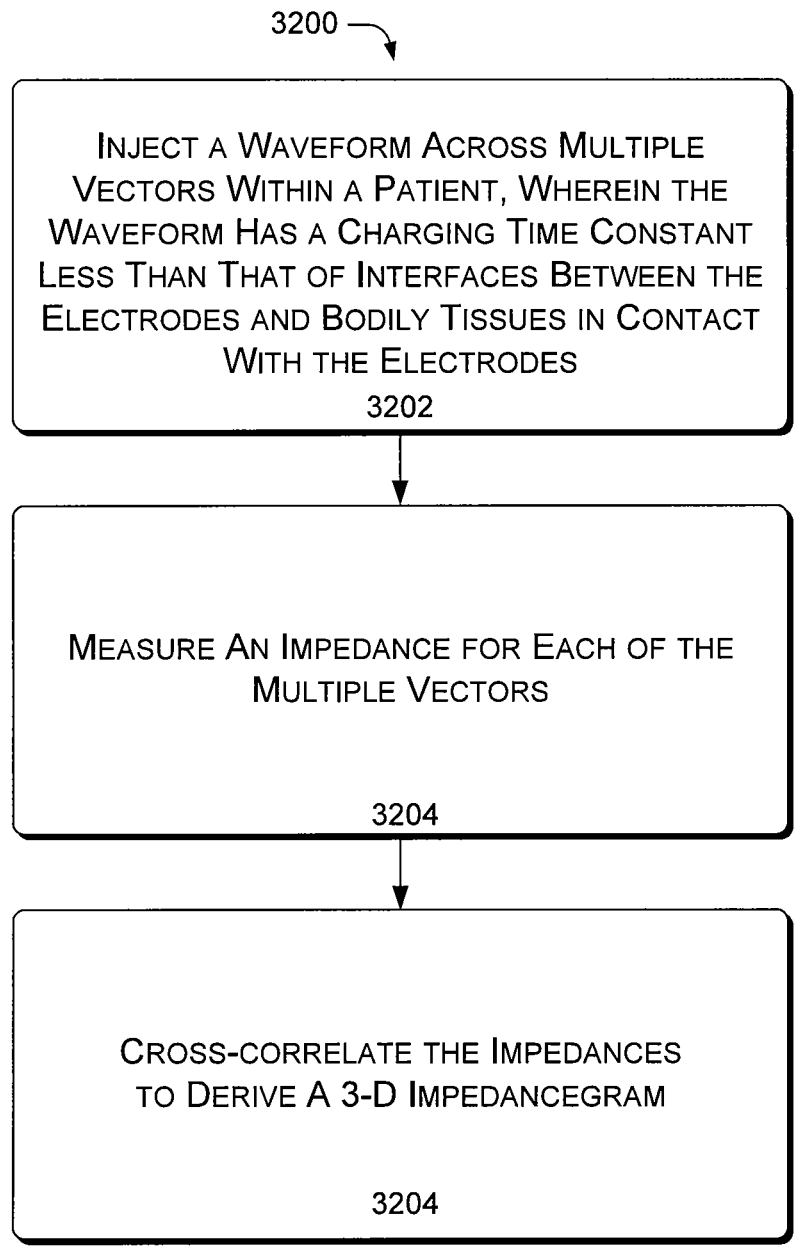
FIG. 32 is a flow diagram of an exemplary method of applying an exemplary waveform over a multi-vector network to obtain a 3-D impedancegram.

FIG. 32 shows an exemplary method 3200 of applying an exemplary waveform over a multi-vector network to obtain a 3-D impedancegram. The exemplary method 3200 may be implemented in connection with many suitably configured implantable devices, although it will be described as being executed by the exemplary multi-vector network engine 438 and/or the exemplary impedance measurement circuit architecture 500. In the flow diagram of FIG. 32, the operations are summarized in individual blocks. Some operations may be performed in hardware and/or as machine-readable instructions (software or firmware) that can be executed by a processor, such as microcontroller 421.

At block 3202, an exemplary waveform 503 is applied across multiple vectors within a patient. The exemplary waveform 503 has a duration less than a charging time constant of the electrode-electrolyte interface between the electrodes of the multi-vector network and the bodily tissue providing the electrolyte.

At block 3204, an impedance is measured and/or calculated for each of the multiple vectors.

At block 3206, the impedances are cross-correlated to form a 3-D impedancegram. The multi-vector network can be selected such that the multiple vectors are positioned for visualizing an area or a volume of tissue or for discerning a rotational vector effect, etc.

Conclusion

Although exemplary systems and methods have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

APPENDIX A

The suggested combinations that will cover the usage of a fully-featured CRT device are:
1. RV coil to Case. This electrode combination represents one of the defibrillation vectors.
2. SVC coil to Case. This electrode combination represents one of the defibrillation vectors.
3. RV coil to SVC coil: This electrode combination may be part of some defibrillation vectors. Additionally, it could also check connectivity at the device header, or abrasion inside the lead.
4. RA ring electrode to Case. This electrode combination could be used for unipolar pacing.
5. RA tip electrode to Case. This electrode combination could be used for unipolar pacing.
6. RV ring electrode to Case. This electrode combination could be used for unipolar pacing.
7. RV tip electrode to Case. This electrode combination could be used for unipolar pacing.
8. LV ring electrode to Case. This electrode combination could be used for unipolar pacing.
9. LV tip electrode to Case. This electrode combination could be used for unipolar pacing.
10. RA ring electrode to RV ring electrode. The pair is involved in A-BiV pacing. Additionally, lead jacket abrasion and header misconnections could be resolved.
11. RA tip electrode to RV tip electrode. The pair is involved in A-BiV pacing. Additionally, lead jacket abrasion and header misconnections could be resolved.
12. RA ring electrode to LV ring electrode. The pair is involved in A-BiV pacing. Additionally, lead jacket abrasion and header misconnections could be resolved.
13. RA tip electrode to LV tip electrode. The pair is involved in A-BiV pacing. Additionally, lead jacket abrasion and header misconnections could be resolved.
14. RV ring electrode to LV ring electrode. The pair is involved in A-BiV pacing. Additionally, lead jacket abrasion and header misconnections could be resolved.
15. RV tip electrode to LV tip electrode. The pair is involved in A-BiV pacing. Additionally, lead jacket abrasion and header misconnections could be resolved.
16. RA ring electrode to RA tip electrode. The pair is involved in bipolar pacing. Additionally, insulation abrasion inside the lead could be resolved.
17. RV ring electrode to RV tip electrode. The pair is involved in bipolar pacing. Additionally, insulation abrasion inside the lead could be resolved.
18. LV ring electrode to LV tip electrode. The pair is involved in bipolar pacing. Additionally, insulation abrasion inside the lead could be resolved.
19. RV coil electrode to RV tip electrode. Insulation abrasion inside the lead could be resolved.
20. RV coil electrode to RV ring electrode. Insulation abrasion inside the lead could be resolved.

What is claimed is:

1. An implantable device, comprising:
multiple electrodes configured to apply a multi-phasic pulse waveform over multiple vectors, wherein the multi-phasic pulse waveform is generated from a source and a sink having different magnitudes;
a waveform generator for generating and applying the multi-phasic pulse waveform over the multiple vectors through tissue of a human being, wherein the multi-phasic pulse waveform has a duration less than a charging time constant of electrode-electrolyte interfaces in the tissue;
an impedance measurement module configured to obtain one impedance measurement for each of the multiple vectors; and
an evaluator configured to process impedance measurements for the multiple vectors in order to estimate a status of a bodily parameter of the human being.

2. The implantable device as recited in claim 1, wherein the bodily parameter comprises heart failure or tissue swelling.

3. The implantable device as recited in claim 1, wherein at least one of the multiple vectors is configured to pass through a heart or a pericardium of the human being and the bodily parameter comprises pulmonary edema.

4. The implantable device as recited in claim 1, further comprising a trender configured to estimate a trend of the bodily parameter over time.

5. The implantable device as recited in claim 4, wherein the trender relates the status of the bodily parameter estimated by the evaluator to a threshold.

6. The implantable device as recited in claim 1, further comprising a diagnostics module configured to evaluate a degree of heart failure based on the status of the bodily parameter.

7. The implantable device as recited in claim 6, wherein the diagnostics module is further configured to monitor a trend of the bodily parameter and to evaluate a progression of heart failure based on the trend of the bodily parameter over time.

8. The implantable device as recited in claim 6, wherein the diagnostics module is further configured to monitor a trend of the bodily parameter and to evaluate a late stage of heart failure based on the status or the trend of the bodily parameter over time.

9. The implantable device as recited in claim 1, further comprising a cross-correlator configured to process the impedance measurements obtained for each of the multiple vectors, wherein the multiple vectors comprise vectors between multiple different sets of electrodes.

10. The implantable device as recited in claim 1, further comprising a vector weighting engine configured to apply a weight to the impedance measurement associated with each vector according to a relevance of each vector to a hemodynamic parameter.

11. The implantable device as recited in claim 1, further comprising an alert module configured to provide a notification of a change in the bodily parameter.

12. The implantable device as recited in claim 11, wherein the notification is provided to the human being via at least one of the implantable device or via a device external to the human being.

13. The implantable device as recited in claim 1, wherein the waveform generator applies the multi-phasic pulse waveform over the multiple vectors between the multiple electrodes that include at least one of:
   a right-atrial-ring-electrode to left-ventricular-ring-electrode vector;
   a left-ventricular-ring-electrode to right-ventricular-ring-electrode vector; or
   a left-ventricular-ring-electrode to case-electrode vector.

14. The implantable device as recited in claim 1, wherein the multi-phasic pulse waveform possesses alternating positive and negative phases and having null phases located between successive ones of the alternating positive and negative phases.

15. An implantable device, comprising:
   a waveform generator for generating and applying a multi-phasic pulse waveform over multiple vectors through tissue of a human being, wherein the multi-phasic pulse waveform possesses alternate positive and negative phases generated by a source and a sink having different magnitudes such that the multi-phasic pulse waveform also possesses an additive net-zero charge and an additive net-zero voltage and has a duration less than a charging time constant of electrode-electrolyte interfaces in the tissue;
   an impedance measurement module configured to obtain one impedance measurement for each of the multiple vectors; and
   an evaluator configured to process impedance measurements for the multiple vectors in order to estimate a status of a bodily parameter of the human being.

16. The implantable device as recited in claim 15, further comprising a trender configured to estimate a trend of the bodily parameter over time.

17. The implantable device as recited in claim 15, further comprising a diagnostics module configured to evaluate a degree of heart failure based on the status of the bodily parameter.

18. The implantable device as recited in claim 15, wherein the waveform generator applies the multi-phasic pulse waveform over multiple vectors that include at least one of:
   a right-atrial-ring-electrode to left-ventricular-ring-electrode vector;
   a left-ventricular-ring-electrode to right-ventricular-ring-electrode vector; or
   a left-ventricular-ring-electrode to case-electrode vector.

19. The implantable device as recited in claim 15, further comprising multiple electrodes configured to apply the multi-phasic pulse waveform over the multiple vectors.

20. The implantable device as recited in claim 15, wherein the multi-phasic pulse waveform possesses alternating positive and negative phases and having null phases located between successive ones of the alternating positive and negative phases.

21. An implantable device, comprising:
   a processing circuit comprising electronics;
   a waveform generator for generating and applying a multi-phasic pulse waveform over multiple vectors through a tissue of a human being, wherein the multi-phasic pulse waveform possesses alternating positive and negative phases and having null phases located between successive ones of the alternating positive and negative phases, the null phases having a duration sufficient to allow the electronics in the processing circuit of the implantable device to settle and the multi-phasic pulse waveform has a duration less than a charging time constant of electrode-electrolyte interfaces in the tissue;
   an impedance measurement module configured to obtain one impedance measurement for each of the multiple vectors; and
   an evaluator configured to process the multiple impedance measurements in order to estimate a status of a bodily parameter of the human being.

22. The implantable device as recited in claim 21, wherein the bodily parameter comprises heart failure or tissue swelling.

23. The implantable device as recited in claim 21, wherein at least one of the multiple vectors passes through a heart or a pericardium of the human being and the bodily parameter comprises pulmonary edema.

24. The implantable device as recited in claim 21, further comprising a vector weighting engine configured to apply a weight to the impedance measurement associated with each vector according to a relevance of each vector to a hemodynamic parameter.

* * * * *